US010399071B2

(12) United States Patent
Hong et al.

(10) Patent No.: US 10,399,071 B2
(45) Date of Patent: Sep. 3, 2019

(54) POLYMER CONTAINING CARBOXYL GROUP, PREPARATION METHOD AND APPLICATION THEREOF, SUPPORTED CATALYST AND PREPARATION METHODS THEREOF AND PREPARATION METHODS OF PENEM ANTIBIOTIC INTERMEDIATE

(71) Applicants: Asymchem Laboratories (Tianjin) Co., Ltd., Tianjin (CN); Asymchem Life Science (Tianjin) Co., Ltd., Tainjin (CN); Tianjin Asymchem Pharmaceutical Co., Ltd., Tianjin (CN); Asymchem Laboratories (Fuxin) Co., Ltd., Fuxin (CN); Jilin Asymchem Laboratories Co., Ltd., Dunhua (CN)

(72) Inventors: Hao Hong, Tianjin (CN); Jiuyuan Li, Tianjin (CN); Changming Dong, Tianjin (CN); Xin Zhang, Tianjin (CN); Gage James, Tianjin (CN)

( * ) Notice: Subject to any disclaimer, the term of this patent is extended or adjusted under 35 U.S.C. 154(b) by 0 days.

(21) Appl. No.: 15/039,189

(22) PCT Filed: Sep. 10, 2014

(86) PCT No.: PCT/CN2014/086240
§ 371 (c)(1),
(2) Date: May 25, 2016

(87) PCT Pub. No.: WO2015/078218
PCT Pub. Date: Jun. 4, 2015

(65) Prior Publication Data
US 2017/0136450 A1 May 18, 2017

(30) Foreign Application Priority Data
Nov. 29, 2013 (CN) .......................... 2013 1 0625973

(51) Int. Cl.
B01J 31/00 (2006.01)
B01J 31/06 (2006.01)
C07D 477/06 (2006.01)
C08F 212/08 (2006.01)
C07D 477/04 (2006.01)
C08F 12/22 (2006.01)
C08F 12/26 (2006.01)
C08F 12/32 (2006.01)
C08F 12/34 (2006.01)
C08F 212/14 (2006.01)
B01J 23/46 (2006.01)
B01J 31/28 (2006.01)
C08J 9/00 (2006.01)
C08J 9/14 (2006.01)

(52) U.S. Cl.
CPC ............. B01J 31/06 (2013.01); B01J 23/464 (2013.01); B01J 31/28 (2013.01); C07D 477/04 (2013.01); C07D 477/06 (2013.01); C08F 12/22 (2013.01); C08F 12/26 (2013.01); C08F 12/32 (2013.01); C08F 12/34 (2013.01); C08F 212/08 (2013.01); C08F 212/14 (2013.01); C08J 9/0061 (2013.01); C08J 9/141 (2013.01); C08J 9/142 (2013.01); C08J 9/145 (2013.01); C08J 9/149 (2013.01); C08J 2203/12 (2013.01); C08J 2203/14 (2013.01); C08J 2203/142 (2013.01); C08J 2325/08 (2013.01); C08J 2405/00 (2013.01); C08J 2429/04 (2013.01); Y02P 20/584 (2015.11)

(58) Field of Classification Search
None
See application file for complete search history.

(56) References Cited

U.S. PATENT DOCUMENTS

| 2008/0039604 | A1 | 2/2008 | Konishi et al. |
| 2008/0182934 | A1 | 7/2008 | Ganapathiappan et al. |
| 2011/0009617 | A1* | 1/2011 | Che ..................... C07C 67/343 540/200 |

FOREIGN PATENT DOCUMENTS

| CN | 1560095 | 1/2005 |
| CN | 103059784 | 4/2013 |
| CN | 103159886 | 6/2013 |
| CN | 103254854 | 8/2013 |
| JP | 61-120139 | 6/1986 |
| WO | WO 2015/078218 | 6/2015 |

OTHER PUBLICATIONS

International Preliminary Report on Patentability dated May 31, 2016 From the International Bureau of WIPO Re. Application No. PCT/CN2014/086240 and Its Translation Into English.
International Search Report and the Written Opinion dated Dec. 16, 2014 From the State Intellectual Property Office of the People's Republic of China Re. Application No. PCT/CN2014/086240 and Its Translation Into English.
Fan et al. "A Novel Method for the Synthesis of 1,4-Bis(4'-Vinylphenoxy) Butane", Chemical Reagents, 28(1): 1-3, Jan. 31, 2006. English Abstract on p. 3.

(Continued)

Primary Examiner — Yun Qian

(57) ABSTRACT

A polymer containing a carboxyl group, a preparation method and an application thereof, a supported catalyst and a preparation method thereof and preparation methods of penem antibiotic intermediate are disclosed. The polymer has high rigidity and hardness, thus the mechanical properties of the polymer is effectively improved. Meanwhile, in the polymer, the carboxyl group is used as a main functional group, and is used as a carrier to prepare, by means of a coordination reaction between the carboxyl group and a heavy metal, a supported metal catalyst which has better connection stability between the metal and the polymer. The above two factors can improve the stability of the supported metal catalyst, such that the catalyst can be recycled without losing the catalytic activity. Meanwhile, loss of a heavy metal active ingredient and production cost can be reduced.

3 Claims, No Drawings

(56) References Cited

OTHER PUBLICATIONS

Supplementary European Search Report and the European Search Opinion dated May 22, 2017 From the European Patent Office Re. Application No. 14865893.3. (6 Pages).
Wolf et al. "Synthese und Prüfung Neuartiger Carboxyl-Ionenaustauscherharze auf Polymerisationsbasis", Zeitschrift für Chemie, XP055370044, 8(1): 26-27, Jan. 2, 1968.

* cited by examiner

POLYMER CONTAINING CARBOXYL GROUP, PREPARATION METHOD AND APPLICATION THEREOF, SUPPORTED CATALYST AND PREPARATION METHODS THEREOF AND PREPARATION METHODS OF PENEM ANTIBIOTIC INTERMEDIATE

RELATED APPLICATIONS

This application is a National Phase of PCT Patent Application No. PCT/CN2014/086240 having International filing date of Sep. 10, 2014, which claims the benefit of priority of Chinese Patent Application No. 201310625973.X filed on Nov. 29, 2013. The contents of the above applications are all incorporated by reference as if fully set forth herein in their entirety.

FIELD AND BACKGROUND OF THE INVENTION

The present disclosure relates to the technical field of chemical synthesis, particularly to a functionalized polymer containing a carboxyl group, a preparation method thereof, and an application thereof in preparing a supported metal catalyst, a supported metal catalyst, and a preparation method of a penem antibiotic intermediate by a carbene insertion reaction catalyzed by a supported metal catalyst.

Since a concept of applying a light divinylbenzene cross-linked chloromethylated polystyrene resin in solid phase peptides synthesis reported by Merrifield for the first time almost half a century ago, it has become more and more common to apply polymers in synthesis and purification of the compounds using different methods. Recently, various macromolecule materials, such as JandaJel and Tentageld have been developed. These materials have been not only applied as carriers of solid phase synthesis, but also used for supported reagents, catalysts and so on. An advantage of these materials over the Merrifield resin is: a reaction center is on a terminal of a polyether chain, which is away from a non-polar polystyrene framework in a resin. Therefore, demands for polymer swelling are somewhat reduced.

Generally, a chiral or achiral ligand (such as a phosphorus ligand and an amino ligand) is connected on a polymer by means of a covalent bond or a non-covalent bond, which is aimed to support a heavy metal catalyst. The polymer is used as a carrier to support the heavy metal catalyst by coordination of the heavy metal catalyst and the ligand on the carrier. The aspect has been widely reported (*Chem. Rev.* 2009, 109, 815), and a formed supported catalyst is able to catalyze a specific reaction, which will be illustrated with an example as follows:

A ketone ester compound shown in the following formula (VI) is prepared by a diazo compound shown in formula (V) under the catalysis of a catalyst 1 (a rhodium catalyst).

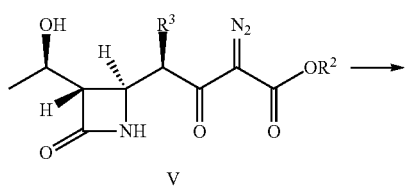

V

-continued

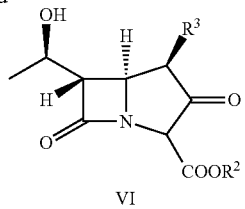

VI

The structural formula of the catalyst 1 is as follows:

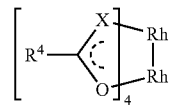

wherein $R^2$ is a protecting group of carboxyl, $R^3$ is hydrogen or methyl, X is an oxygen atom or a nitrogen atom substituted by an alkyl group, and $R^4$ is an alkyl radical substituted appropriately.

Specifically, the diketone ester compound shown in the foregoing formula (VI) is prepared by the diazo compound shown in formula (V) through an N—H insertion reaction. The reaction applies a rhodium catalyst compound shown above as a catalyst. The rhodium catalyst compound is able to form a rhodium carbene with the compound shown in the formula (V), which can release a diazo radical at the same time to form a product (VI) eventually. The product is an important penem antibiotic intermediate.

However, a supported metal catalyst prepared using the polymer having the phosphorus ligand and the amino ligand and so on as a catalyst carrier has the following disadvantages: (1) poor chemical properties to result in easy loss of the catalyst, and a high loss rate of an expensive heavy metal supported thereon; (2) low yield of preparation of the catalyst; (3) generally low catalytic activity of the catalyst. The catalytic activity, mechanical properties and so on of the catalyst have a direct impact on the cost of industrial production especially when the expensive heavy metals supported in the catalyst comprising rhodium and so on.

SUMMARY OF THE INVENTION

The present disclosure aims to provide a polymer containing a carboxyl group, a preparation method and an application thereof, and preparation methods of a supported catalyst and a penem antibiotic intermediate, so as to solve the problems of loss of a heavy metal and high production cost caused by poor mechanical properties of a supported metal catalyst in the prior art.

To achieve the purpose above, according to an aspect of the present disclosure, a polymer containing a carboxyl group is provided. The polymer is prepared by polymerizing the following monomers with molar percentage: (1) 50%~99% of a monomer A; (2) 0.5%~25% of a monomer B; (3) 0.5%~25% of a monomer C, wherein the monomer A has a structure shown in formula (I):

I in the monomer A, R is phenyl or COOR', and R' is C1~C10 alkyl;

the monomer B has one of structure shown in formula (II-1) to (II-8):

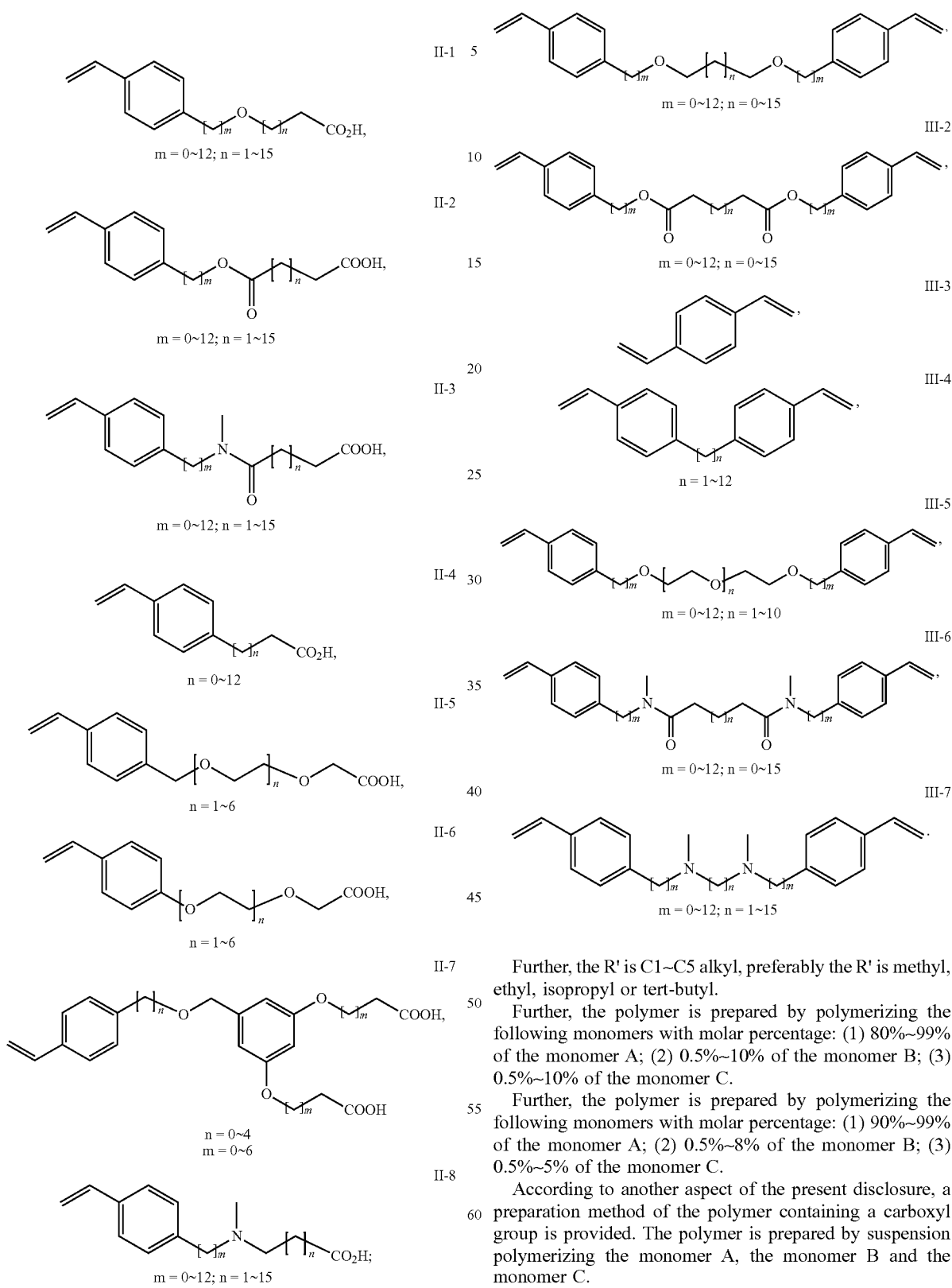

the monomer C has one of structures shown in formula (III-1) to (III-7):

Further, the R' is C1~C5 alkyl, preferably the R' is methyl, ethyl, isopropyl or tert-butyl.

Further, the polymer is prepared by polymerizing the following monomers with molar percentage: (1) 80%~99% of the monomer A; (2) 0.5%~10% of the monomer B; (3) 0.5%~10% of the monomer C.

Further, the polymer is prepared by polymerizing the following monomers with molar percentage: (1) 90%~99% of the monomer A; (2) 0.5%~8% of the monomer B; (3) 0.5%~5% of the monomer C.

According to another aspect of the present disclosure, a preparation method of the polymer containing a carboxyl group is provided. The polymer is prepared by suspension polymerizing the monomer A, the monomer B and the monomer C.

Further, the polymer is prepared by suspension polymerizing the monomer A, the monomer B and the monomer C in an aqueous medium with the presence of an initiator, a stabilizer and a pore-foaming agent.

Further, the initiator is azodiisobutyronitrile or Benzoyl Peroxide (BPO), and a molar quantity of the initiator accounts for 0.05%~10% of a total molar quantity of the monomer A, and the monomer B and the monomer C.

Further, the stabilizer is a mixture comprised of a water-soluble polymer and an inorganic salt; preferably, a mass ratio of the water-soluble polymer to the inorganic salt is 0.2~5:1; the water-soluble polymer is polyvinyl alcohol or Arabic gum; the inorganic salt is sodium chloride; a mass concentration of the water-soluble polymer in the aqueous medium is 0.1%~10%, and a mass concentration of the inorganic salt in the aqueous medium is 0.2%~20%.

Further, the pore-foaming agent is one or more selected from toluene, xylene, chlorobenzene and Tetrahydrofuran (THF), and a mass ratio of the pore-foaming agent to a total amount of the monomer A, and the monomer B and the monomer C is 0.1~3:1.

According to still another aspect of the present disclosure, a use of the polymer containing a carboxyl group as a carrier of a supported metal catalyst is provided.

Further, the supported metal catalyst is a supported rhodium catalyst, a supported palladium catalyst, a supported platinum catalyst, a supported ruthenium catalyst or a supported iridium catalyst.

According to still another aspect of the present disclosure, a supported metal catalyst is provided, wherein the polymer above is used as a carrier of the supported metal catalyst.

Further, the supported metal catalyst is a supported rhodium catalyst, a supported palladium catalyst, a supported platinum catalyst, a supported ruthenium catalyst or a supported iridium catalyst.

Further, the supported metal catalyst is a supported rhodium catalyst having a structure shown in the following formula (IV):

IV wherein $R^1$ is C1~C10 alkyl, preferably $R^1$ is methyl, ethyl, tert-butyl, n-hexyl or n-heptyl; P—COO— is a residue of the polymer with hydrogen removed, and x is any number of 0.1~4.0.

According to still another aspect of the present disclosure, a preparation method of the supported metal catalyst is provided. The supported metal catalyst is prepared by a reaction between the polymer above and an organic acid salt of rhodium, an equation of the reaction is as follows:

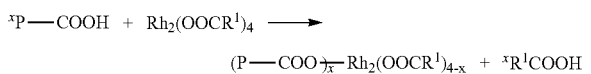

wherein P—COOH is the claimed polymer, x is any number of 0.1~4.0, $R^1$ is C1~C10 alkyl, preferably is methyl, ethyl, tert-butyl, n-hexyl or n-heptyl.

Further, the reaction is carried out in an organic solvent, and the organic solvent is selected from tetrahydrofuran (THF), toluene, xylene, chlorobenzene or diethylene glycol dimethyl ether.

According to still another aspect of the present disclosure, a method for preparing a penem antibiotic intermediate through a carbene insertion reaction is provided. Under the catalysis of the supported rhodium catalyst above, the penem antibiotic intermediate shown in formula (VI) is prepared by a reaction of the compound shown in formula (V), and an equation of the reaction is as follows:

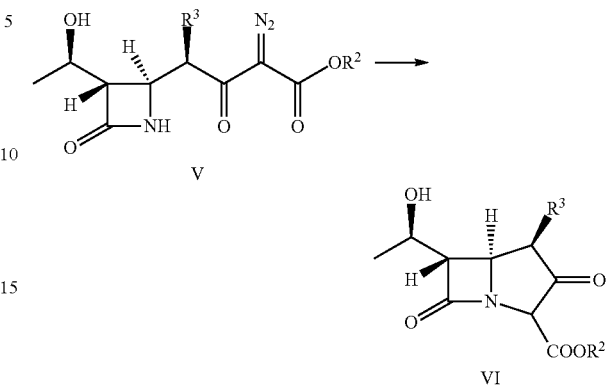

wherein R2 is p-nitrobenzyl, 2-nitrobenzyl, 3-nitrobenzyl, benzyl, p-chlorobenzyl, p-methylbenzyl, allyl, methyl or ethyl, and R3 is hydrogen or methyl.

Further, the reaction is carried out in an organic solvent, and the organic solvent is selected from ethyl acetate, methyl acetate, isopropyl acetate, 1,4-dioxane, tetrahydrofuran (THF), methyl tert-butyl ether (MTBE), ether, dichloromethane or 1,2-dichloroethane.

Further, a molar ratio of the supported metal catalyst to the compound shown in formula (V) is 1:50~2000.

Further, a reaction temperature is 20° C.~50° C.

A polymer containing a carboxyl group, a preparation method and an application thereof, and preparation methods of a supported catalyst and a penem antibiotic intermediate have been provided by the present disclosure. The polymer containing a carboxyl group provided by the present disclosure is a cross-linked polymer, a polymer chain of whom contains a large amount of benzene rings, which can improve the rigidity and hardness of the polymer, thus effectively improving the mechanical properties of the polymer. Meanwhile, in the polymer, the carboxyl group is used as a main functional group. A supported metal catalyst, which using the polymer as a carrier and is prepared by means of a coordination reaction between the carboxyl group and a heavy metal, has better connection stability between the metal and the polymer. The two factors above can improve the stability of the supported metal catalyst, thus the catalyst can be recycled without losing the catalytic activity. Meanwhile, loss of a heavy metal active ingredient and production cost can be reduced.

DESCRIPTION OF SPECIFIC EMBODIMENTS OF THE INVENTION

It needs to be noted that the embodiments in the application and the characteristics in the embodiments may be combined with each other if there is no conflict. The present disclosure will be expounded hereinafter with reference to the embodiments.

As introduced in the background, an existing supported metal catalyst has problems including loss of a heavy metal and high production cost caused by poor mechanical properties. To solve the problems, a polymer containing a carboxyl group is provided by the present disclosure. The polymer is prepared by polymerizing the following monomers with molar percentage: (1) 50%~99% of a monomer A;

(2) 0.5%~25% of a monomer B; (3) 0.5%~25% of a monomer C, wherein the monomer A has a structure shown in formula (I):

I in the monomer A, R is phenyl or COOR', and R' is C1~C10 alkyl;

the monomer B has one of structures shown in formula (II-1) to (II-8):

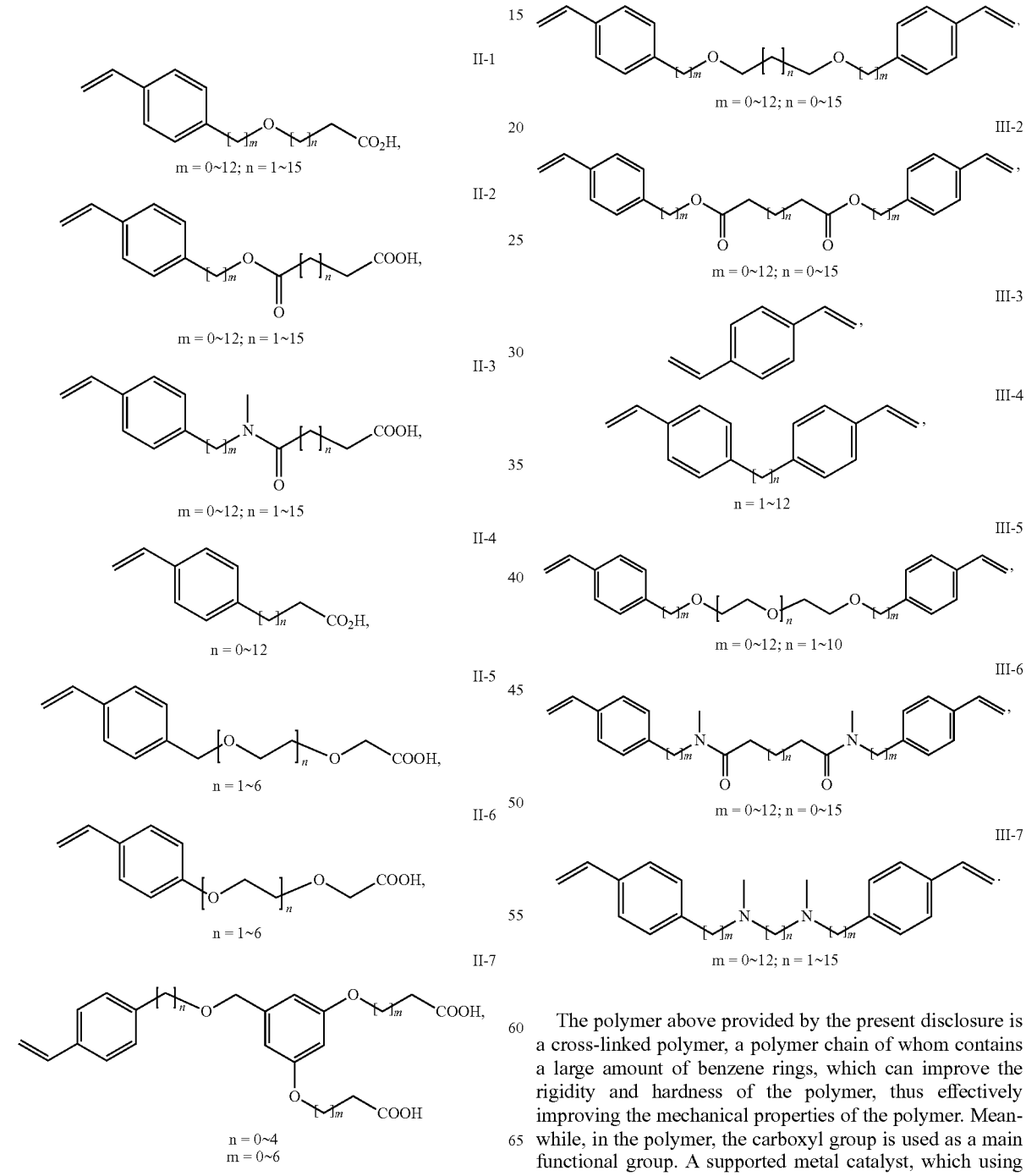

the monomer C has one of structures shown in formula (III-1) to (III-7):

The polymer above provided by the present disclosure is a cross-linked polymer, a polymer chain of whom contains a large amount of benzene rings, which can improve the rigidity and hardness of the polymer, thus effectively improving the mechanical properties of the polymer. Meanwhile, in the polymer, the carboxyl group is used as a main functional group. A supported metal catalyst, which using the polymer as a carrier and is to prepared by means of a coordination reaction between the carboxyl group and a heavy metal, has better connection stability between metal atoms and the polymer. The two factors above can improve the stability of the supported metal catalyst, thus the catalyst can be recycled without losing the catalytic activity. Meanwhile, loss of a heavy metal active ingredient and production cost can be reduced. Besides, the catalytic activity of the catalyst formed by supporting the metal on the polymer is high, which is more beneficial for improving the reaction yield.

R' in the monomer A of the present disclosure may be selected according to the range above. In a preferred embodiment, the R' is C1~05 alkyl, preferably the R' is methyl, ethyl, isopropyl or tert-butyl. The introduction of the R' enables entrance to some saturated side chains on a rigid polymer molecular chain. Thus can adjusting the flexibility of the molecular chain and the distance between chains, and further adjusting the mechanical properties of a final catalyst. When the R' in the range above is introduced, the mechanical properties of the final catalyst can improve. In the meanwhile, a certain distance between chains can also promote an entrance of metal atoms, which leads a relatively high metal load of the final catalyst.

In the polymer provided by the present disclosure, the mechanical properties of the polymer can be improved to a certain extent as long as the molecular chain includes the three monomers above. In a preferred embodiment, the polymer is prepared by polymerizing the following monomers with molar percentage: (1) 80%~99% of the monomer A; (2) 0.5%~10% of the monomer B; (3) 0.5%~10% of the monomer C. The proportion of the benzene rings and the content of the carboxyl group in the main chain of the polymer can be adjusted by adjusting the use amounts of the three monomers, thus further adjusting the mechanical properties of the polymer and the amount of the metal can be supported by the polymer. By controlling the proportions of the monomers within the ranges above, consideration may be given to the mechanical properties and the amount of the supported metal of the final catalyst. More preferably, the polymer is prepared by polymerizing the following monomers with molar percentage: (1) 90%~99% of the monomer A; (2) 0.5%~8% of the monomer B; (3) 0.5%~5% of the monomer C.

According to another aspect of the present disclosure, a preparation method of the polymer containing a carboxyl group is provided. The polymer is prepared by suspension polymerizing the monomer A, the monomer B and the monomer C. When a suspension polymerization is applied, a solvent is used as a reaction medium, which can improve the reaction stability and conversion rate. In the meanwhile, the suspension polymerization can provide a homogeneous system for the reaction, and a formed polymer product has narrow distribution of molecular weight and high quality.

In a preferred embodiment, the polymer is prepared by suspension polymerizing the monomer A, the monomer B and the monomer C in an aqueous medium with the presence of an initiator, a stabilizer and a pore-foaming agent. The pore-foaming agent can promote a gap formed in a prepared polymer substrate, so that the polymer substrate has a relatively high specific surface area, thereby improving the amount of the metal supported by the final supported catalyst, and improving the catalytic activity of the catalyst.

The initiator, the stabilizer and the pore-forming agent may apply reagents commonly used by those skilled in the art in organic synthesis. In a preferred embodiment, the initiator is, but not limited to azodiisobutyronitrile or Benzoyl Peroxide (BPO), and a molar quantity of the initiator accounts for 0.05%~10% of a total molar quantity of the monomer A, and the monomer B and the monomer C. The stabilizer is, but not limited to a mixture comprised of a water-soluble polymer and an inorganic salt. Preferably, a mass ratio of the water-soluble polymer to the inorganic salt is 0.2~5:1; the water-soluble polymer is polyvinyl alcohol or Arabic gum; the inorganic salt is sodium chloride; a mass concentration of the water-soluble polymer in the aqueous medium is 0.1%~10%, and a mass concentration of the inorganic salt in the aqueous medium is 0.2%~20%. The pore-foaming agent is, but not limited to one or more selected from toluene, xylene, chlorobenzene and tetrahydrofuran (THF); and a mass ratio of the pore-foaming agent to the total amount of the monomer A, and the monomer B and the monomer C is 0.1~3:1.

According to still another aspect of the present disclosure, a use of the polymer containing a carboxyl group as a carrier of a supported metal catalyst is provided. Using the polymer as a carrier, the supported metal catalyst prepared has relatively high mechanical properties. In the meanwhile, a metal is supported on a polymer substrate by means of a coordination reaction between the carboxyl group and the metal, thereby improving the support stability of the metal, and the catalyst can maintain relatively high catalytic activity in a long time during a recycling process.

In the supported metal catalyst, the supported metal may be a metal well known by those skilled in the art. In a preferred embodiment, the supported metal catalyst is a supported rhodium catalyst, a supported palladium catalyst, a supported platinum catalyst, a supported ruthenium catalyst or a supported iridium catalyst.

According to still another aspect of the present disclosure, a supported metal catalyst is provided, wherein the polymer is used as a carrier of the supported metal catalyst.

Preferably, the supported metal catalyst is a supported rhodium catalyst, a supported palladium catalyst, a supported platinum catalyst, a supported ruthenium catalyst or a supported iridium catalyst.

Supported metal catalysts of the types above have relatively high mechanical properties and catalytic activity. In a preferred embodiment, the supported metal catalyst is a supported rhodium catalyst having a structure shown in the following formula (IV):

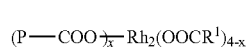

$$(P\text{---}COO)_{\overline{x}}Rh_2(OOCR^1)_{4-x} \qquad \text{IV}$$

wherein $R^1$ is C1~C10 alkyl, preferably $R^1$ is methyl, ethyl, tert-butyl, n-hexyl or n-heptyl; P—COO— is a residue of the polymer with hydrogen removed, and x is any number of 0.1~4.0. Metal rhodium is used as an active ingredient of the catalyst, which is beneficial to achieve a high yield when matched with the polymer. In the meanwhile, support stability between rhodium atoms and the polymer carrier may be better.

According to still another aspect of the present disclosure, a preparation method of the supported metal catalyst is provided. The supported metal catalyst is prepared by a reaction between the polymer above and an organic acid salt of rhodium. In the reaction, hydrogen atoms in the carboxyl functional group carried in the polymer are replaced with metal atoms in the organic acid salt, so as to support the metal atoms on the polymer carrier. An equation of the reaction is as follows:

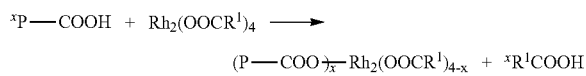

wherein P—COOH is the claimed polymer above, x is any number of 0.1~4.0, $R^1$ is C1~C10 alkyl, preferably $R^1$ is methyl, ethyl, tert-butyl, n-hexyl or n-heptyl. A supported rhodium catalyst formed by the reaction above has relatively high catalytic activity. In the meanwhile, metal rhodium is supported on the polymer carrier with a relatively strong binding force by the carboxyl group, so that the catalyst may be recycled with little loss and high catalytic activity.

According to the above teachings of the present disclosure, a skilled in the art may select a specific process for preparing a catalyst. In a preferred embodiment, the reaction is carried out in an organic solvent. The organic solvent is selected from tetrahydrofuran, toluene, xylene, chlorobenzene or diethylene glycol dimethyl ether.

According to still another aspect of the present disclosure, a method for preparing a penem antibiotic intermediate through a carbene insertion reaction is provided. Under the catalysis of the supported rhodium catalyst above, the penem antibiotic intermediate shown in formula (VI) is prepared by a reaction of a compound shown in formula (V), and an equation is as follows:

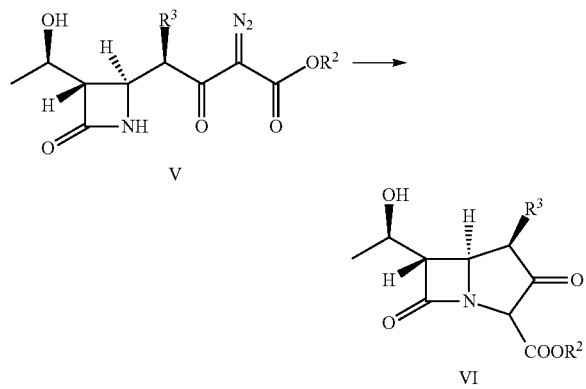

wherein R2 is p-nitrobenzyl, 2-nitrobenzyl, 3-nitrobenzyl, benzyl, p-chlorobenzyl, p-methylbenzyl, allyl, methyl or ethyl, and R3 is hydrogen or methyl.

Using the polymer provided by the present disclosure as a carrier, the supported rhodium catalyst prepared has relatively high mechanical properties and catalytic activity. The reaction yield is high when the penem antibiotic intermediate (formula VI) is prepared by the reaction catalyzed by the supported rhodium catalyst. In the meanwhile, cause of the high mechanical properties, the catalyst may be recycled without loss of activity and the expensive metal active ingredient. Thus the supported rhodium catalyst is more applicable to various reaction, just like batch reactions, a continuous mobile phase reaction and on so. In a word, the reaction cost can be evidently reduced, the production efficiency can be improved and environmental pollution can be reduced compared with an existing preparation method.

Technical conditions commonly used by a skilled in the art may be applied in the method for preparing the penem antibiotic intermediate. In a preferred embodiment, the reaction is carried out in an organic solvent. The organic solvent is selected from ethyl acetate, methyl acetate, isopropyl acetate, 1,4-dioxane, tetrahydrofuran, methyl tert-butyl ether, ether, dichloromethane or 1,2-dichloroethane.

Preferably, a molar ratio of the supported metal catalyst to the compound shown in formula (V) is 1:5~2000.

Preferably, a reaction temperature is 20~50° C.

According to the above teachings of the present disclosure, a skilled in the art have the ability to select a specific operation process for preparing the penem antibiotic intermediate (formula IV). The method is applicable to the batch reactions and the continuous mobile phase reaction.

Specifically, a flow of the batch reactions is as follows: the supported rhodium catalyst is mixed with the organic solvent and stirred for 0~2 hours; a reaction substrate (the compound shown in formula (V)) is added subsequently, the reaction temperature is controlled at 10~120° C., and the reaction time is 0.5~24 hours (depending on a reaction condition); then, filtering and separating are performed to obtain the supported rhodium catalyst; the supported rhodium catalyst is washed by an appropriate solvent, dried and directly used in a reaction of the next cycle, and a filtrate is directly used in a reaction of the next step.

Wherein the molar ratio of the reaction substrate to the catalyst (calculated by Rh) is 50~2000:1; and the use amount of the reaction solvent is 5~30 mL/g relative to the reaction substrate.

A flow of the continuous reaction is as follows: the supported rhodium catalyst is mixed with the organic solvent and stirred for 0~2 hours; a certain volume of an inert filler is added, uniformly stirred with the catalyst, and filled into a tubular reactor with a jacket by a wet method; hot water is introduced as a heat-conducting medium into the jacket of the reactor, the temperature is controlled at 10° C.~120° C.; the reaction substrate is mixed with the organic solvent and stirred until a homogeneous phase is obtained, and the homogeneous phase is pumped into the tubular reactor continuously by a charge pump, and received continuously by a receiver at a receiving end, and a received liquid may be directly used in a reaction of the next step.

Wherein the space velocity of a solution of the reaction substrate is 0.01~0.1 mL/(min·mg Rh). The space velocity mentioned here refers the amount of the solution processed by a unit mass of the catalyst in a time unit. The use amount of the reaction solvent is 5~30 mL/g relative to the reaction substrate. The volume ratio of the inert filler to the catalyst is 0.5~5:1.

In a word, the polymer provided by the present disclosure is a cross-linked polymer which is prepared with a simple and convenient method. The polymer has high carboxyl content, and can effectively support a metal salt to prepare a supported catalyst. The obtained catalyst has good activity and is easy to recycle.

A supported metal catalyst provided by the present disclosure is prepared with a simple and convenient method. It has high content of a supported metal and high binding efficiency, and can be recycled without losing the catalytic activity and is convenient to recycle. Thereby reducing the use amount of the catalyst, effectively saving reaction cost and reducing environmental pollution.

The method provided by the present disclosure to prepare the penem antibiotic intermediate through the carbene insertion reaction applies the supported metal catalyst, which has high catalytic activity and is convenient to recycle and reuse. The method is applicable to various reaction, just like batch reactions, a continuous mobile phase reaction and on so. The reaction cost can be evidently reduced, the production efficiency can be improved and environmental pollution can be reduced compared with an existing preparation method.

The present disclosure will be further expounded below in combination with specific embodiments and these embodiments should not be understood as limitation to the protection scope claimed by the present disclosure.

Unless specified otherwise, all experimental substances are commercialized.

Different polymers containing a carboxyl group are prepared in Embodiment 1 to 11.

Embodiment 1

Monomer Synthesis

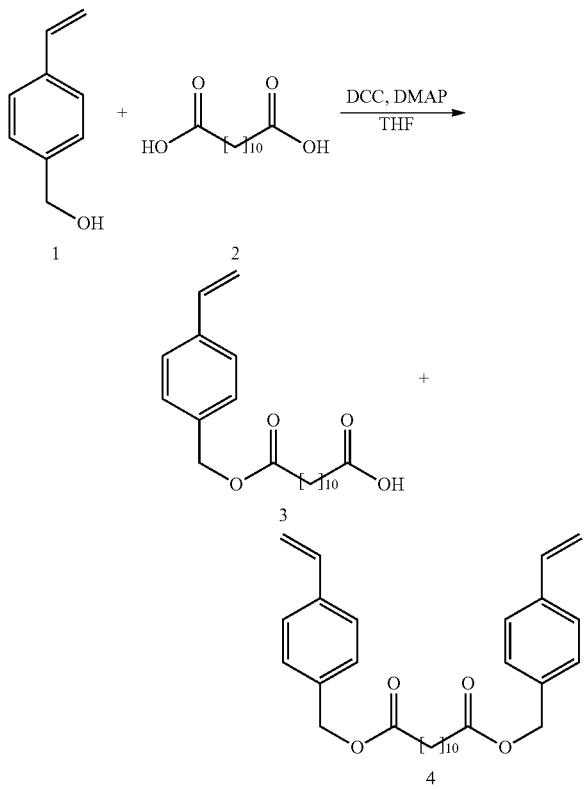

Copolymerization

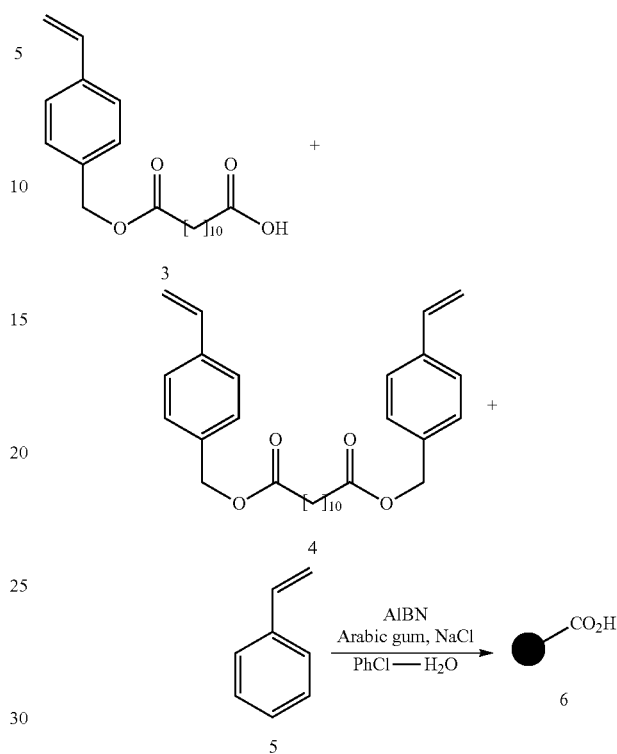

At room temperature, dicyclohexyl carbodiimide (32.1 g, 156 mmol) is added to a THF (300 mL) solution of 4-vinylbenzyl alcohol (1, 20 g, 149 mmol), dodecanedioic acid (2, 30 g, 149 mmol) and 4-dimethylaminopyridine (1.82 g, 14.9 mmol) by batches; stirring is performed continuously at room temperature for 6 hours, and filtering is performed to remove an insoluble substance; a filtrate is concentrated, and a remainder is dissolved by ethyl acetate (300 mL), washed by hydrochloric acid (100 mL×2) with a concentration of 1N, dried with anhydrous sodium sulfate and then depressurized and concentrated; a remainder is purified by silica gel column chromatography to obtain a compound 3 (22.4 g, yield 43%) and a compound 4 (15.6 g, yield 45%).

Compound 3: $^1$H NMR (CDCl$_3$, 400 MHz): δ 1.24-1.36 (m, 12H), 1.57-1.68 (m, 4H), 2.31-2.38 (m, 4H), 5.10 (s, 2H), 5.26 (d, J=10.9 Hz, 1H), 5.75 (d, J=17.6 Hz, 1H), 6.71 (dd, J=17.6, 10.9 Hz, 1H), 7.31 (d, J=8.1 Hz, 2H), 7.40 (d, J=8.1 Hz, 2H).

Compound 4: $^1$H NMR (CDCl$_3$, 400 MHz): δ 1.25-1.35 (m, 12H), 1.59-1.69 (m, 4H), 2.35 (t, J=7.5 Hz, 4H), 5.10 (s, 4H), 5.26 (d, J=10.9 Hz, 2H), 5.76 (d, J=17.6 Hz, 2H), 6.72 (dd, J=17.6, 10.9 Hz, 2H), 7.31 (d, J=8.1 Hz, 4H), 7.40 (d, J=8.1 Hz, 4H).

At room temperature, Arabic gum (8.84 g), sodium chloride (44.2 g) and water (880 mL) are added into a 2 L four-neck flask mounted with a mechanical stirrer, and nitrogen is blown for 3 hours; then a chlorobenzene (147.4 g) solution of styrene (5, 57.5 g, 552 mmol), a monomer (3, 9.15 g, 26.4 mmol), a monomer (4, 7.03 g, 15.2 mmol) and 2,2-azobisisobutyronitrile (AIBN) (586 mg, 3.57 mmol) is depressurized and degassed for three times by an oil pump, and then added to a violently agitated aqueous phase; a reaction solution is heated to 80° C. and stirred for 20 hours to obtain a white solid; the white solid is filtered, washed by water (1000 mL×2) and methyl alcohol (1000 mL) respectively, then extracted and washed by THF (1000 mL) for 10 hours in a Soxhlet extractor, and dried in vacuum to obtain a polymer 6 (51.2 g, yield 69%), which has a theoretical carboxyl content of 0.358 mmol/g. The main particle size of the polymer in a dry state is in a range of 100~900 μm.

The actual carboxyl content may be measured indirectly: using lithium triethylborohydride to reduce a monomer into 12-hydroxyldodecyl carboxylic acid, such as the following: 1.0 g of the polymer 6 is suspended in 25 mL of THF, stood for 30~40 minutes and then cooled to 0° C.; 10 mL of a THF solution of lithium triethylborohydride with a concentration of 1N is dropped in a stirring condition, the temperature is increased to room temperature and stirring is performed overnight; a mixed solution of 5 mL of acetic acid and 5 mL of water is added to the system to quench the reaction; filtering is performed to remove a solid, and concentration is performed to remove THF; 30 mL of a sodium hydroxide solution having a concentration of 1N is added to the system, washing is performed with MTBE; an aqueous phase is regulated at pH≤4 using hydrochloric acid with a concentration of 2N, then extracted by dichloromethane, and concentrated to obtain 81 mg of a white solid; it is measured by ¹H Nuclear Magnetic Resonance (NMR) that the content of obtained 12-hydroxyldodecyl carboxylic acid is 84%, and it is thereby calculated that the carboxyl content in the polymer is 0.314 mmol/g (a calculation method: 81×0.84/216.17/1.0).

Polymer 6, FT-IR (KBr, cm⁻¹): 3416, 3083, 3060, 2920, 2851, 1636, 1601, 1130, 757, 696. There is no absorption peak around 1800 cm⁻¹, which indicates that double bonds have been fully polymerized.

Embodiment 2

Monomer Synthesis

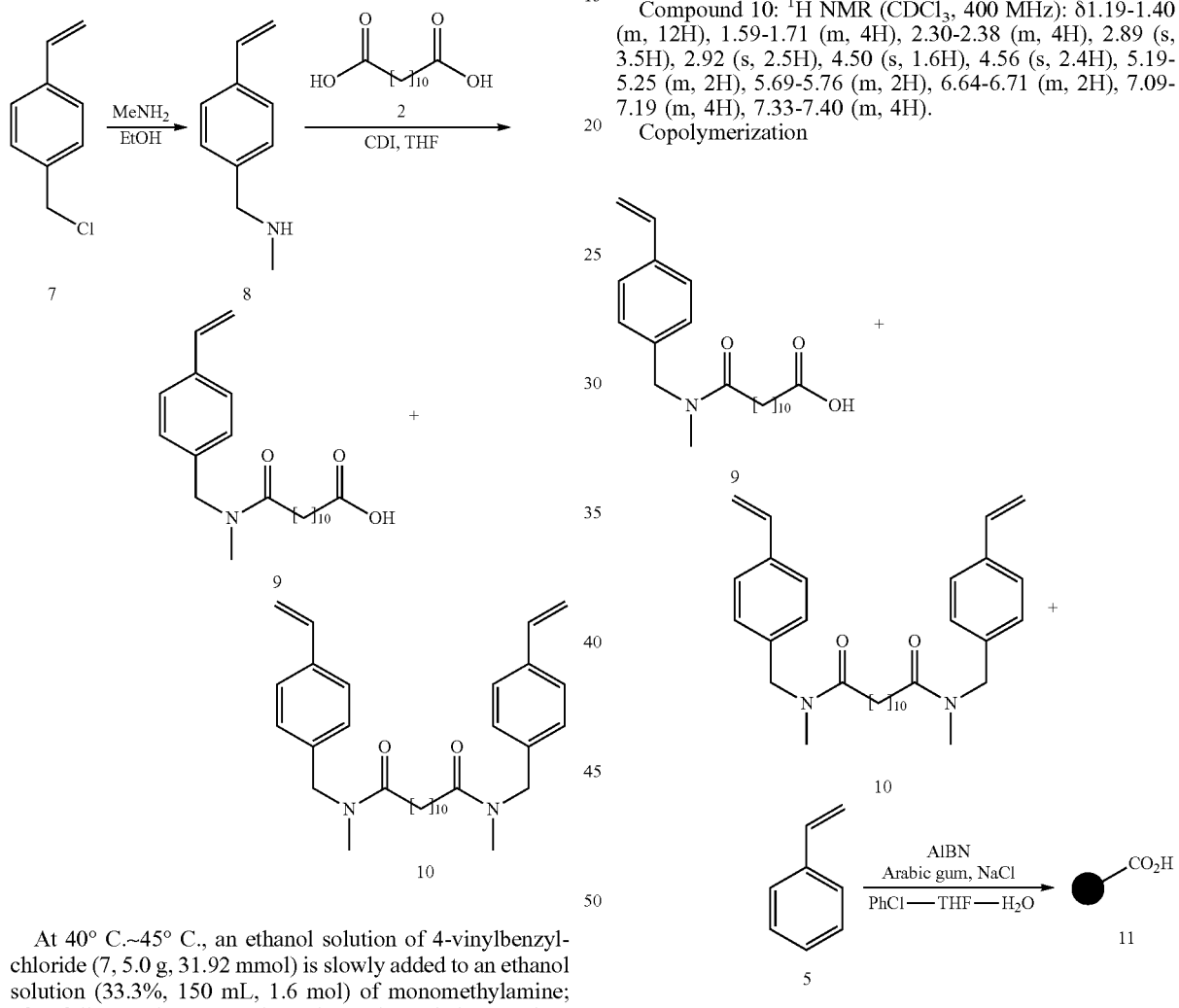

At 40° C.~45° C., an ethanol solution of 4-vinylbenzylchloride (7, 5.0 g, 31.92 mmol) is slowly added to an ethanol solution (33.3%, 150 mL, 1.6 mol) of monomethylamine; after fully reacting, a reaction mixture is cooled, potassium carbonate (6.62 g, 47.9 mmol) is added and stirred sequentially for 1 hour; filtering is performed to remove a solid, and a filtrate is concentrated to obtain a crude product (¹H NMR yield: 52%) of a red oily compound 8, which is directly used in a reaction of the next step.

Compound 8: ¹H NMR (CDCl₃, 400 MHz): δ2.45 (s, 3H), 3.74 (s, 2H), 5.22 (d, J=10.9 Hz, 1H), 5.73 (d, J=17.6 Hz, 1H), 6.71 (dd, J=17.6, 10.9 Hz, 1H), 7.27 (d, J=7.9 Hz, 2H), 7.37 (d, J=7.9 Hz, 2H).

At room temperature, dodecanedioic acid (2, 20.6 g, 89.5 mmol) is dissolved in THF (350 mL), dicarbonylimidazole (29.0 g, 179 mmol) is also added by batches, and stirring is performed sequentially for 1 hour; the compound 8 (12.5 g, ¹H NMR content, 84.9 mmol) is added subsequently; a reaction is carried out at room temperature for 4 hours, concentration is performed, and a crude product is dissolved with ethyl acetate (200 mL), and then washed by hydrochloric acid (50 mL×2) with a concentration of 3N and a saturated brine (100 mL), dried with anhydrous sodium sulphate, filtered to remove the drying agent and concentrated; a crude product is purified by silica gel column chromatography to obtain a white solid compound 9 (14.7 g, yield 48%) and a compound 10 (9.84 g, yield 45%).

Compound 9: ¹H NMR (d₆-DMSO, 400 MHz): δ1.20-1.30 (m, 12H), 1.42-1.55 (m, 4H), 2.16-2.20 (m, 4H), 2.80 (s, 1.1H), 2.88 (s, 1.9H), 4.47 (s, 1.3H), 4.54 (s, 0.7H), 5.21-5.25 (m, 1H), 5.77-5.83 (m, 1H), 6.67-6.75 (m, 1H), 7.13-7.17 (m, 2H), 7.40-7.47 (m, 2H), 11.98 (s, 1H).

Compound 10: ¹H NMR (CDCl₃, 400 MHz): δ1.19-1.40 (m, 12H), 1.59-1.71 (m, 4H), 2.30-2.38 (m, 4H), 2.89 (s, 3.5H), 2.92 (s, 2.5H), 4.50 (s, 1.6H), 4.56 (s, 2.4H), 5.19-5.25 (m, 2H), 5.69-5.76 (m, 2H), 6.64-6.71 (m, 2H), 7.09-7.19 (m, 4H), 7.33-7.40 (m, 4H).

Copolymerization

At room temperature, Arabic gum (12 g), sodium chloride (60 g) and water (1200 mL) are added into a 3 L four-neck flask mounted with a mechanical stirrer, nitrogen is blown for 3 hours; a chlorobenzene (179.5 g) and THF (29.2 g) solution of styrene (5, 82.4 g, 791.7 mmol), a monomer (9, 13.7 g, 38.1 mmol), a monomer (10, 8.70 g, 17.8 mmol) and AIBN (835 mg, 5.08 mmol) is depressurized and degassed for three times by an oil pump, and then added to a violently agitated aqueous phase; a reaction solution is heated to 80° C. and stirred for 20 hours to obtain a white solid; the white solid is filtered, washed by water (1200 mL×2) and methanol (1200 mL) respectively, then extracted and washed by THF (1200 mL) for 10 hours in a Soxhlet extractor, and dried in vacuum to obtain a polymer 11 (75.1 g, yield 72%), which has a theoretical carboxyl content of 0.365 mmol/g. The main particle size of the polymer in a dry state is in a range of 200~800 μm.

It is measured by element analysis that C: 88.75%, H: 7.935% and N: 0.99%, therefore the content of O is 2.325% and it is thus calculated that the actual carboxyl content is 0.373 mmol/g.

Polymer 11, FT-IR (KBr, cm$^{-1}$): 3417, 3082, 3025, 2920, 2850, 1648, 1601, 1452, 757, 694. There is no absorption peak around 1800 cm$^{-1}$, which indicates that double bonds have been fully polymerized.

Embodiment 3

Monomer Synthesis

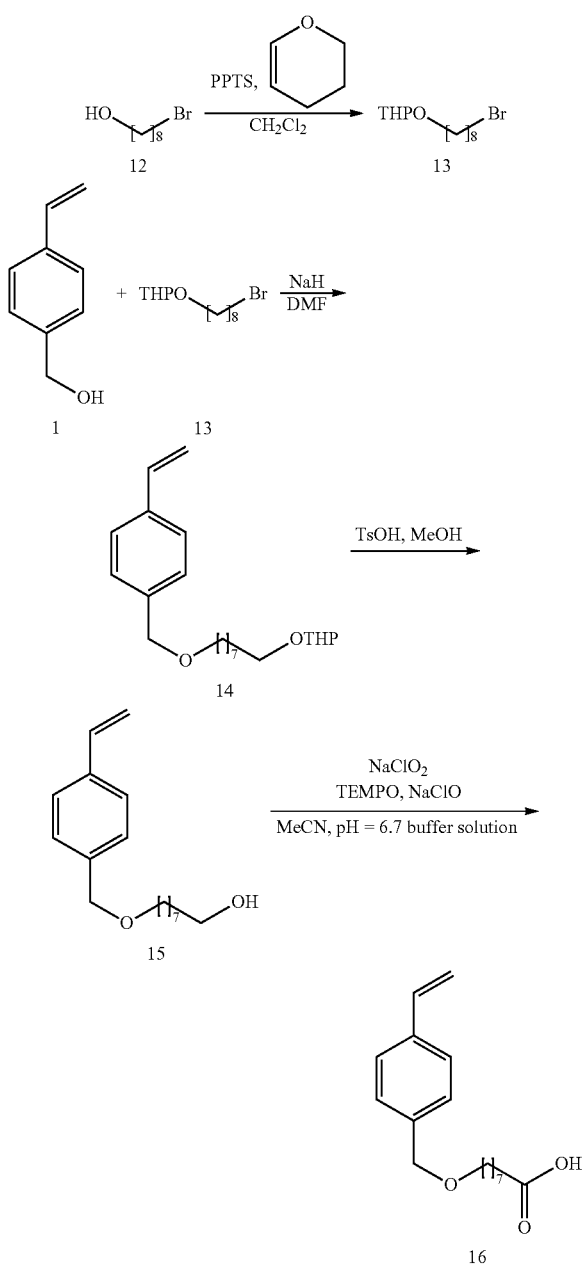

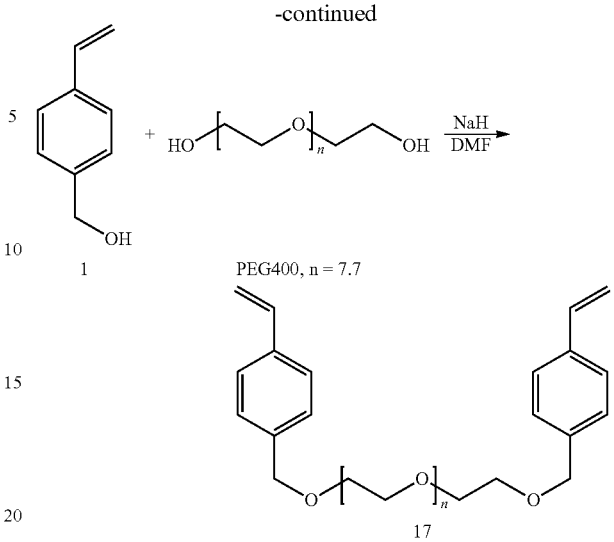

Synthesis of Compound 13

At room temperature, a dichloromethane (110 mL) solution of 8-bromo-1-octanol (12, 11.0 g, 52.6 mmol), dihydropyran (22.1 g, 263 mmol), and pyridinium p-toluenesulfonate (528.7 mg, 2.1 mmol) is added to a reaction flask in turn, stirred at room temperature until being reacted completely; a reaction solution is concentrated until there is no fraction, and a crude product is purified by silica gel column chromatography to obtain a yellow oily compound 13 (14.1 g, yield 89%).

Compound 13: $^1$H NMR (CDCl$_3$, 400 MHz): δ1.28-1.46 (m, 8H), 1.48-1.62 (m, 6H), 1.66-1.74 (m, 1H), 1.79-1.87 (m, 3H), 3.34-3.41 (m, 3H), 3.46-3.51 (m, 1H), 3.69-3.75 (m, 1H), 3.83-3.88 (m, 1H), 4.55-4.57 (m, 1H).

Synthesis of Compound 16

In an ice-water bath, a Dimethyl Formamide (DMF) (2 mL) solution of 4-vinylbenzyl alcohol (1, 4.0 g, 29.8 mmol) is added into a DMF (36 mL) suspension of NaH (content 60%, 1.30 g, 32.4 mmol), and then stirred in the ice-water bath for 15 minutes; the compound 13 (7.92 g, 27.0 mmol) is dissolved in DMF (2 mL) and added to a reaction solution, and the reaction solution is heated to room temperature, stirred sequentially for 4 hours, and then cooled by an ice-water bath; the reaction is quenched by saturated ammonium chloride; extraction is performed using EtOAc (3×40 mL); organic phases are combined, washed by a saturated brine (40 mL), dried by anhydrous sodium sulfate and filtered to remove the drying agent, a filtrate is concentrated, and a crude product is purified by silica gel column chromatography to remove a large-polarity substance, thereby obtaining a colourless oily compound 14 (8.0 g, crude yield 85%).

A crude product (8.0 g, 23.0 mmol) of the compound 14 is dissolved in methanol (80 mL), p-toluenesulfonic acid (158 mg, 0.92 mmol) is added, stirring is performed at room temperature until a reaction is carried out completely, a reaction solution is concentrated and a crude product is purified by silica gel column chromatography to obtain a white solid compound 15 (4.34 g, yield 72%).

The compound 15 (4.34 g, 16.5 mmol) and a 2,2,6,6-tetramethylpiperidinyloxy, free radical (TEMPO) (181 mg, 1.16 mmol) are suspended in acetonitrile (80 mL), and a buffer salt (60 mL, 0.67N, pH=6.7) of sodium hydrogen phosphate and sodium dihydrogen phosphate, and heated to 35° C.; an aqueous solution (13 mL) of sodium chlorite (3.32 g, 33.1 mmol) and a diluted sodium hypochlorite solution (0.13 mL of sodium hypochlorite with a concentration of 9% is diluted to 4.1 mL, 2.0 mol %) are slowly added into the reaction system at the same time within 0.5 hours, stirred at 35° C. until a reaction is carried out completely; then the reaction system is cooled to room temperature, water (30 mL) is added, and the pH value of the system is regulated at 8.0 using a sodium hydroxide solution with a concentration of 2N; an obtained white solid is filtered, and washed by MTBE (20 mL×3); a solid is collected, and suspended in MTBE (40 mL) and water (30 mL); the pH value of an phase is regulated at 3~4 using hydrochloric acid with a concentration of 2N; standing is performed to separate organic phases, and aqueous phases are extracted by MTBE (20 mL); organic phases are combined, dried by anhydrous sodium sulfate, and filtered to remove the drying agent; a filtrate is concentrated to obtain a white solid compound 16 (3.64 g, yield 80%).

Compound 16: $^1$H NMR (CDCl$_3$, 400 MHz): δ1.30-1.42 (m, 6H), 1.58-1.68 (m, 4H), 2.33-2.38 (m, 2H), 3.44-3.47 (m, 2H), 4.50 (s, 2H), 5.24 (d, J=10.9 Hz, 2H), 5.75 (d, J=17.1 Hz, 1H), 6.72 (dd, J=17.6, 10.9 Hz, 1H), 7.30 (d, J=7.8 Hz, 2H), 7.40 (d, J=8.1 Hz, 2H).

Compound 17 is prepared by polyethylene glycol 400 with reference to a literature (*J. Org. Chem.* 1996, 61, 8321-8324), which has an average n=7.7 and an average molecular weight of 634.34.

Copolymerization

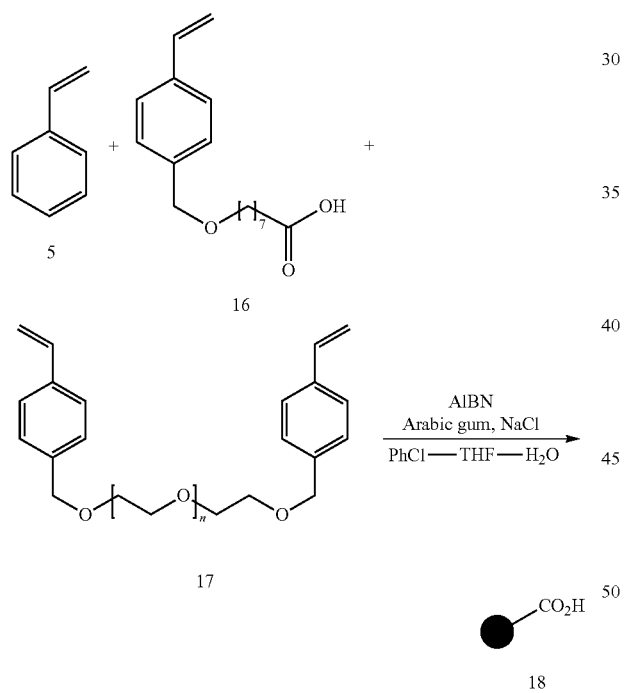

At room temperature, Arabic gum (0.58 g), sodium chloride (2.9 g) and water (58 mL) are added into a 250 mL four-neck flask mounted with a mechanical stirrer, nitrogen is blown for 3 hours; a chlorobenzene (4.15 g) solution of styrene (5, 3.5 g, 33.6 mmol), a monomer (16, 497 mg, 1.8 mmol), a monomer (17, 155 mg, 0.24 mmol) and AIBN (35.6 mg, 0.22 mmol) is depressurized and degassed for three times by an oil pump, and then added to a violently agitated aqueous phase; a reaction solution is heated to 80° C. and stirred for 20 hours to obtain a white solid; the white solid is filtered, washed by water (80 mL×2) and methanol (80 mL) respectively, then extracted and washed by THF (80 mL) for 10 hours in a Soxhlet extractor, and dried in vacuum to obtain a polymer 18 (2.5 g, yield 60%), which has a theoretical carboxyl content of 0.433 mmol/g. The main particle size of the polymer in a dry state is in a range of 100~750 μm.

The actual carboxyl content is measured by the following method:

At room temperature, 1.0 g of the compound 18 is suspended in 40 mL of dichloromethane, and stood for 30~40 minutes; then 2.0 g of benzylamine, 220 mg of 4-dimethylaminopyridine, and 1.87 g of triethylamine are added in a stirring condition, 3.56 g of 1-Ethyl-3-(3-dimethylaminopropyl)carbodiimide hydrochloride (EDCl) is added by batches finally, and stirring is performed overnight; the system is subjected to suction filtration, and washed by dichloromethane, THF, methanol, water and methanol in turn; an obtained polymer is further reacted twice in the same conditions, and a finally-obtained polymer is depressurized and dried overnight at 40° C.~50° C.

It is measured by element analysis that the content of each element is as follows: C: 89.30%, H: 7.836% and N: 0.56%. The calculated O content is 2.308%. It is calculated that the molar content of N atoms is 0.400 mmol/g (a calculation process: 0.56/14/1), and it is corrected that the actual carboxyl content is 0.386 mmol/g.

Polymer 18, FT-IR (KBr, cm$^{-1}$): 3413, 3060, 3001, 2923, 2852, 1704, 1654, 1617, 1495, 756. There is no absorption peak around 1800 cm$^{-1}$, which indicates that double bonds have been fully polymerized.

Embodiment 4

Monomer Synthesis

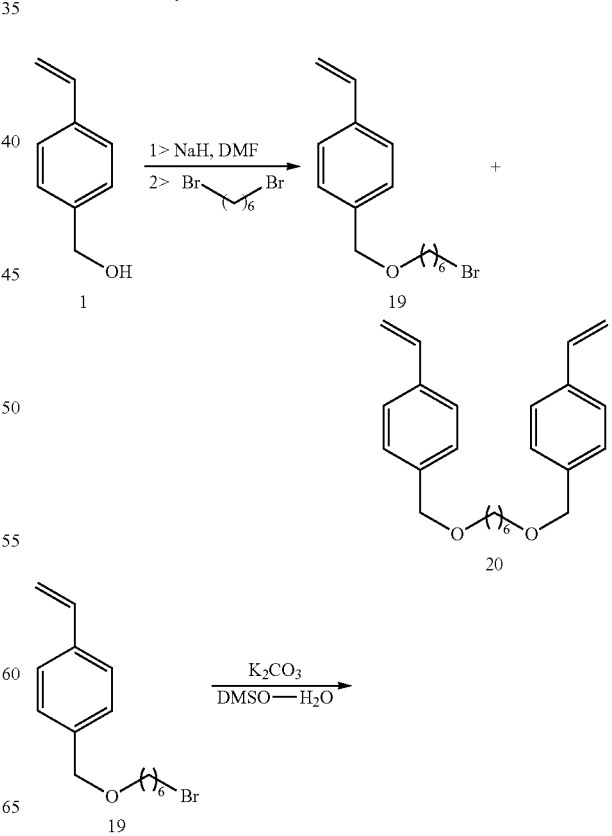

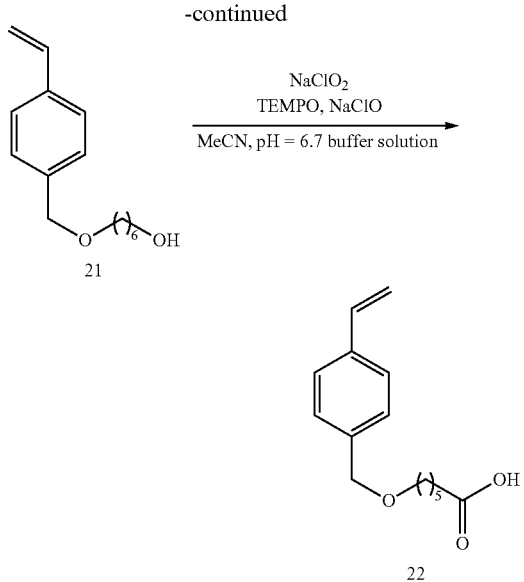

Synthesis of Compounds 19 and 20

At room temperature, sodium hydride (content 60%, 7.15 g, 178.7 mmol) and DMF (80 mL) are added into a reaction flask, and cooled to 0° C.; a DMF (20 mL) solution of p-vinylbenzyl alcohol (1, 20 g, 149.0 mmol) is dropped; after the dropping, stirring is performed sequentially for 30 minutes, and then a DMF (20 mL) solution of 1,6-dibromohexane (36.3 g, 149.0 mmol) is dropped; after the dropping, the reaction is heated to room temperature and stirring is performed sequentially for 5 hours; saturated ammonium chloride is added to quenched the reaction, extraction is performed by MTBE; organic phases are combined, washed by a saturated brine, dried by anhydrous sodium sulfate, filtered to remove the drying agent, depressurized and concentrated until there is no fraction; a crude product is purified by silica gel column chromatography to obtain a compound 19 (15.9 g, yield 36%) and a compound 20 (3.91 g, yield 15%).

NMR of the Compound 19 and the compound 20 is consistent with that reported in a literature (*Angew. Chem., Int. Ed.* 2010, 49, 6979-6983).

Synthesis of Compound 22

At room temperature, the compound 19 (12 g, 40.0 mmol) and dimethyl sulfoxide (36 mL) are added into a reaction flask, then an aqueous (12 mL) solution of potassium carbonate (11.1 g) is added, heated to 80° C. and stirred for 20 hours; the temperature is reduced to room temperature, and water is added to perform dilution, and then extraction is performed by ethyl acetate; organic phases are combined, washed by saturated ammonium chloride, dried by anhydrous sodium sulfate, filtered to removed the drying agent, depressurized and concentrated until there is no fraction; a crude product is purified by silica gel column chromatography to obtain a compound 21 (7.1 g, yield 75%).

The compound 21 (6.8 g, 29 mmol) and TEMPO (318 mg, 2 mmol) are suspended in acetonitrile (120 mL), and a buffer salt (90 mL, 0.67N, Ph=6.7) of sodium hydrogen phosphate and sodium dihydrogen phosphate, and heated to 35° C.; an aqueous solution (22 mL) of sodium chlorite (5.25 g, 58 mmol) and a diluted sodium hypochlorite solution (0.23 mL of sodium hypochlorite with a concentration of 9% is diluted to 7.2 mL, 2.0 mol %) are slowly added into the reaction system at the same time within 0.5 hours, stirred at 35° C. until a reaction is carried out completely, and cooled to room temperature; water (30 mL) is added, and the pH value is regulated at 8.0 by a sodium hydroxide solution with a concentration of 2N; an obtained white solid is filtered, and washed by MTBE (30 mL×3); a solid is collected, and suspended in MTBE (60 mL) and water (40 mL); the pH value of an aqueous phase is regulated at 3~4 by hydrochloric acid with a concentration of 2N; standing is performed to separate organic phases; the aqueous phase is extracted by MTBE (30 mL); the organic phases are combined, dried by anhydrous sodium sulfate, and filtered to remove the drying agent; a filtrate is concentrated to obtain a white solid compound 22 (3.64 g, yield 77%).

Compound 22: $^1$H NMR (CDCl$_3$, 400 MHz): δ1.28-1.35 (m, 2H), 1.56-1.66 (m, 5H), 2.33-2.36 (m, 2H), 3.45-3.47 (m, 2H), 4.50 (s, 2H), 5.18 (d, J=10.7 Hz, 1H), 5.70 (d, J=17.6 Hz, 1H), 6.69 (dd, J=17.6, 10.7 Hz, 1H), 7.27 (d, J=7.8 Hz, 2H), 7.30 (d, J=7.8 Hz, 2H).

Copolymerization

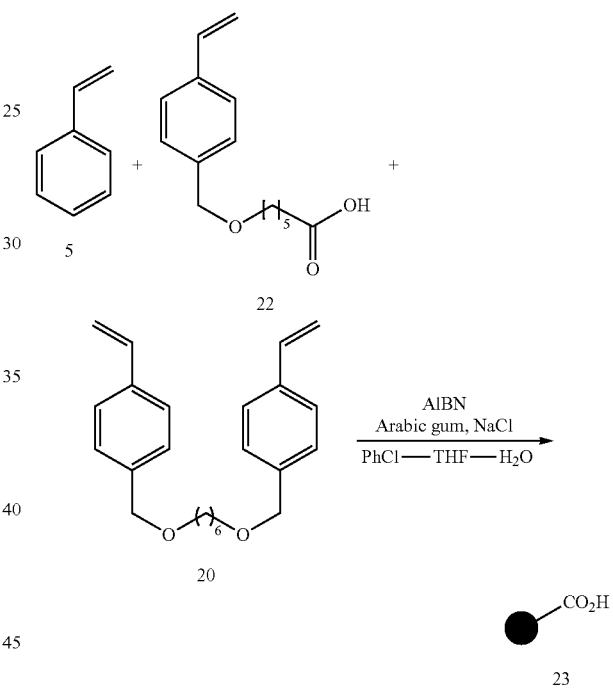

At room temperature, Arabic gum (1.5 g), sodium chloride (3.0 g) and water (150 mL) are added into a 500 mL four-neck flask mounted with a mechanical stirrer, nitrogen is blown for 5 hours; a chlorobenzene (9.0 g) and THF (1.0 g) solution of styrene (5, 5 g, 48 mmol), a monomer (22, 640 mg, 2.58 mmol), a monomer (20, 350 mg, 1.03 mmol) and AIBN (250.8 mg, 0.3 mmol) is depressurized and degassed for three times by an oil pump, and then added to a violently agitated aqueous phase; a reaction solution is heated to 80° C. and stirred for 20 hours; an obtained white solid is filtered, washed by water (100 mL×2) and methanol (100 mL) respectively, then extracted and washed by THF (100 mL) for 10 hours in a Soxhlet extractor, and dried in vacuum to obtain a polymer 23 (4.40 g, yield 75%), which has a theoretical carboxyl content of 0.433 mmol/g. The main particle size of the polymer in a dry state is in a range of 100~750 μm.

The carboxyl content is measured according to the following method:

At room temperature, 1.0 g of the compound 23 is suspended in 40 mL of dichloromethane, and stood for 30~40 minutes; then 2.0 g of benzylamine, 220 mg of 4-dimethylaminopyridine and 1.87 g of triethylamine are added in a stirring condition, and 3.56 g of EDCl is added by batches finally; stirring is performed overnight; the system is subjected to suction filtration, and washed by dichloromethane, THF, methanol, water and methanol in turn; an obtained polymer is further reacted twice in the same conditions, and a finally-obtained polymer is depressurized and dried overnight at 40° C.~50° C.

It is measured by element analysis that the content of each element is as follows: C: 89.89%, H: 7.735% and N: 0.54%. The calculated O content is 1.835%. It is calculated that the molar content of N atoms is 1.835 mmol/g (a calculation process: 0.54/14/1), and it is corrected that the actual carboxyl content is 0.378 mmol/g.

Polymer 23, FT-IR (KBr, cm$^{-1}$): 3413, 3025, 2922, 2851, 1653, 1601, 1493, 1452, 695. There is no absorption peak around 1800 cm$^{-1}$, which indicates that double bonds have been fully polymerized.

Embodiment 5

Monomer Synthesis

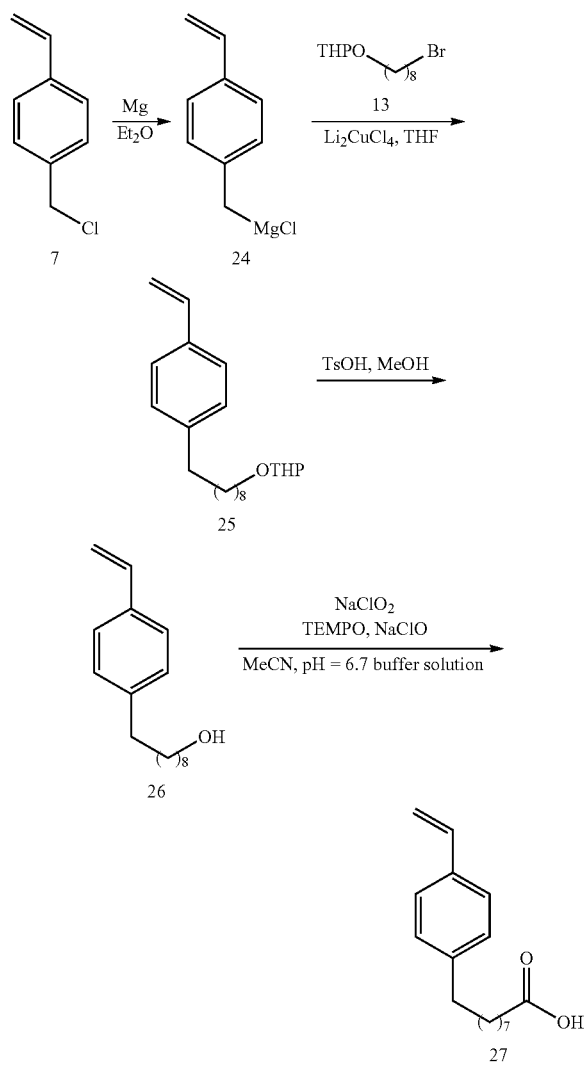

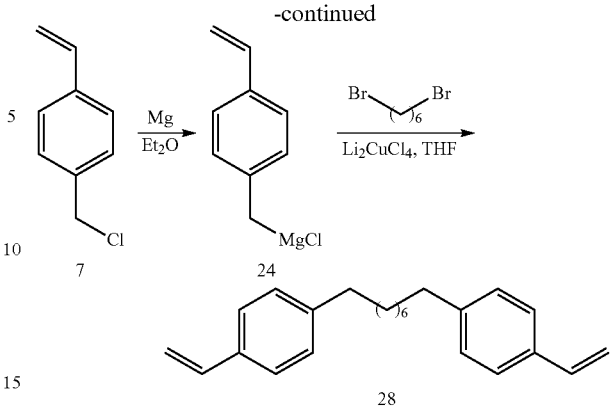

Synthesis of Compound 27

At room temperature, magnesium chips (7.07 g, 295 mmol) and ether (12 mL) are added to a reaction flask, then p-vinylbenzyl chloride (7.15 g, 98.3 mmol) is dissolved in 100 mL of ether, about 6% of the solution is added and heated slightly to cause a reaction, then the remaining solution is slowly dropped into the reaction system while the reaction system is maintain boiled slightly; after the dropping, the reaction system is stirred for 0.5 hour at 38° C.~40° C., then cooled to room temperature and stood for further use.

The compound 13 (19.2 g, 65.5 mmol) and THF (40 mL) are added to a reaction flask at room temperature, then a THF solution (2.6 mL, 2.6 mmol) of lithium tetrachlorocuprate is added, and cooled to 0° C.; an ether solution of the freshly prepared compound 24 above is dropped after the dropping, the temperature is increased to room temperature naturally to carry out a reaction for 24 hours; the reaction is quenched by saturated ammonium chloride with a volume of 15 times, and filtering is performed through a layer of diatomite to remove a generated solid, and then extraction is performed by MTBE; organic phases are combined, washed by a saturated brine, dried by anhydrous sodium sulfate, filtered to remove the drying agent, depressurized and concentrated until there is no fraction to obtain a crude product (17.4 g) of a compound 25 which is directly used in a reaction of the next step.

The crude product (17.4 g) of the compound 25 is dissolved in methanol (160 mL), p-toluene sulphonic acid (564 mg, 3.27 mmol) is added, stirring is performed at room temperature until a reaction is carried out completely; a reaction solution is concentrated and a crude product is purified by silica gel column chromatography to obtain a compound 26 (11.0 g, yield 68%).

The compound 26 (10 g, 40.6 mmol) and TEMPO (445 mg, 2.85 mmol) are suspended in acetonitrile (180 mL), and a buffer salt (135 mL, 0.67N, pH=6.7) of sodium hydrogen phosphate and sodium dihydrogen phosphate, and heated to 35° C.; an aqueous solution (32 mL) of sodium chlorite (8.16 g, 81.5 mmol) and a diluted sodium hypochlorite solution (0.32 mL of a sodium hypochlorite solution with a concentration of 9% is diluted to 10 mL, 2.0 mol %) are slowly added into the reaction system at the same time within 0.5 hours, stirred at 35° C. until a reaction is carried out completely, and cooled to room temperature; water (80 mL) is added, and the pH value is regulated at 8.0 by a sodium hydroxide solution with a concentration of 2N; an obtained white solid is filtered, and washed by MTBE (50 mL×3); a solid is collected, and suspended in MTBE (100 mL) and water (80 mL); the pH value of an aqueous phase is regulated at 3~4 by hydrochloric acid with a concentration of 2N; standing is performed to separate organic phases; the aqueous phase is extracted by MTBE (40 mL); the organic phases are combined, dried by anhydrous sodium sulfate, and filtered to remove the drying agent; a filtrate is concentrated to obtain a compound 27 (8.98 g, yield 85%).

Compound 27: $^1$H NMR (CDCl$_3$, 400 MHz): δ1.25-1.34 (m, 8H), 1.56-1.66 (m, 4H), 2.34 (t, J=7.5 Hz, 2H), 2.58 (t, J=7.7 Hz, 2H), 5.18 (d, J=10.7 Hz, 1H), 5.70 (d, J=17.6 Hz, 1H), 6.69 (dd, J=17.6, 10.9 Hz, 1H), 7.13 (d, J=7.7 Hz, 2H), 7.32 (d, J=7.6 Hz, 2H).

Synthesis of Compound 28

Magnesium chips (7.07 g, 295 mmol) and ether (12 mL) are added to a reaction flask at room temperature, then p-vinylbenzyl chloride (7, 15 g, 98.3 mmol) is dissolved in 100 mL of ether, about 6% of the solution is added and heated slightly to cause a reaction, then the remaining solution is slowly dropped into the reaction system while the reaction system is maintain boiled slightly; after the dropping, the reaction system is stirred for 0.5 hour at 38° C.~40° C., cooled to room temperature and stood for further use.

1,6-dibromohexane (6.0 g, 24.6 mmol) and THF (20 mL) are added to a reaction flask at room temperature, then a THF solution (2 mL, 2 mmol) of lithium tetrachlorocuprate is added, and cooled to 0° C.; an ether solution of the freshly prepared compound 24 above is dropped; after the dropping, the temperature is increased to room temperature naturally to carry out a reaction for 24 hours; the reaction is quenched by saturated ammonium chloride with a volume of 15 times, and filtering is performed through a layer of diatomite to remove a generated solid, and then extraction is performed by MTBE; organic phases are combined, washed by a saturated brine, dried by anhydrous sodium sulfate, filtered to remove the drying agent, depressurized and concentrated until there is no fraction; a crude product is purified by silica gel column chromatography to obtain a compound 28 (5.95 g, yield 76%).

Compound 28: $^1$H NMR (CDCl$_3$, 400 MHz): δ1.24-1.36 (m, 8H), 1.57-1.65 (m, 4H), 2.60 (t, J=7.6 Hz, 4H), 5.20 (d, J=10.6 Hz, 2H), 5.71 (d, J=17.5 Hz, 2H), 6.71 (dd, J=17.5, 10.6 Hz, 2H), 7.15 (d, J=7.9 Hz, 4H), 7.34 (d, J=7.9 Hz, 4H).

Copolymerization

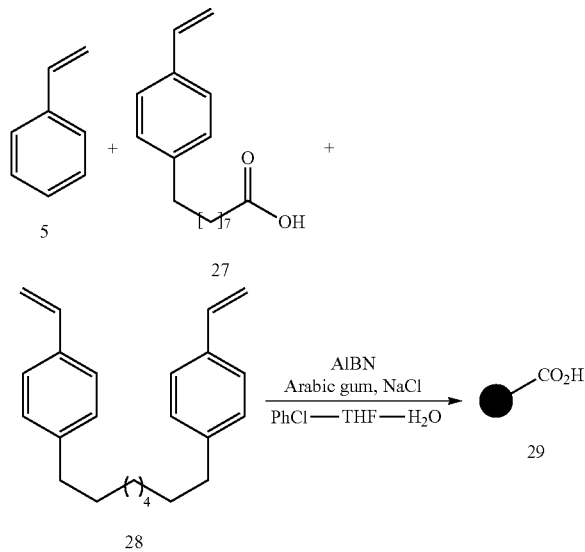

At room temperature, Arabic gum (1.3 g), sodium chloride (2.6 g) and water (130 mL) are added into a 500 mL four-neck flask mounted with a mechanical stirrer, nitrogen is blown for 5 hours; a chlorobenzene (6.2 g) and THF (1.2 g) solution of styrene (5, 5 g, 48 mmol), a monomer (27, 747 mg, 2.87 mmol), a monomer (28, 414 mg, 1.30 mmol) and AIBN (50.8 mg, 0.3 mmol) is depressurized and degassed for three times by an oil pump, and then added to a violently agitated aqueous phase; a reaction solution is heated to 80° C. and stirred for 20 hours; an obtained white solid is filtered, washed by water (100 mL×2) and methanol (100 mL) respectively, then extracted and washed by THF (100 mL) for 10 hours in a Soxhlet extractor, and dried in vacuum to obtain a polymer 29 (4.31 g, yield 70%), which has a theoretical carboxyl content of 0.465 mmol/g. The main particle size of the polymer in a dry state is in a range of 150~750 μm.

Measured values of element analysis: C: 90.07%, H: 8.259%, and the obtained O content is 1.671%. Therefore the actual carboxyl content is about 0.522 mmol/g.

Polymer 29, FT-IR (KBr, cm$^{-1}$): 3418, 3026, 2922, 2851, 1705, 1493, 1452, 697. There is no absorption peak around 1800 cm$^{-1}$, which indicates that double bonds have been fully polymerized.

Embodiment 6

Monomer Synthesis

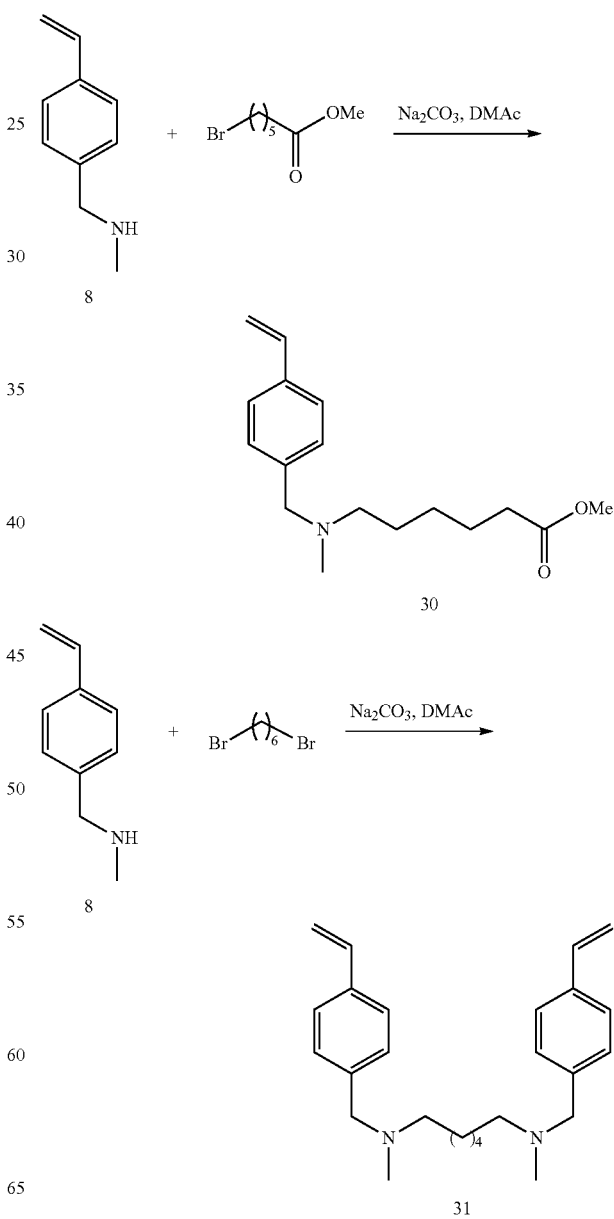

Synthesis of Compound 30

Synthesis of the compound 8 is the same as that in Embodiment 2.

The crude product of the compound 8 (9.57 g, 65 mmol, obtained according to the theoretical yield of the last step), sodium carbonate (14.4 g, 135.8 mmol), methyl 6-bromohexanoate (16.3 g, 78 mmol) and N,N-dimethylacetamide (50 mL) are added to a reaction flash at room temperature; a reaction solution is heated to 75° C. to react for 16 hours, diluted by water and extracted by ethyl acetate; organic phases are combined, washed by a saturated brine, dried by anhydrous sodium sulfate, filtered to remove the drying agent, depressurized and concentrated until there is no fraction; a crude product is purified by silica gel column chromatography to obtain a compound 30 (9.84 g, yield 55%).

Compound 30: $^1$H NMR (CDCl$_3$, 400 MHz): δ1.27-1.37 (m, 2H), 1.51 (dd, J=14.8, 7.5 Hz, 2H), 1.62 (dd, J=15.2, 7.6 Hz, 2H), 2.17 (s, 3H), 2.32 (dt, J=15.2, 7.4 Hz, 4H), 3.45 (s, 2H), 3.66 (s, 3H), 5.21 (d, J=10.9 Hz, 1H), 5.72 (d, J=17.6 Hz, 1H), 6.70 (dd, J=17.7, 10.9 Hz, 1H), 7.25 (d, J=8.1 Hz, 2H), 7.35 (d, J=8.1 Hz, 2H).

Synthesis of Compound 31

The crude product of the compound 8 (9.27 g, 63 mmol, obtained according to the theoretical yield of the last step), sodium carbonate (14.6 g, 138 mmol), 1,6-dibromohexane (5.12 g, 21 mmol) and N,N-Dimethylformamide (50 mL) are added to a reaction flash at room temperature; a reaction solution is heated to 75° C. to react for 16 hours, then diluted by water and extracted by ethyl acetate; organic phases are combined, washed by a saturated brine, dried by anhydrous sodium sulfate, filtered to remove the drying agent, depressurized and concentrated until there is no fraction; a crude product is purified by silica gel column chromatography to obtain a compound 31 (3.88 g, yield 49%).

Compound 31: $^1$H NMR (CDCl$_3$, 400 MHz): δ1.27-1.34 (m, 4H), 1.46-1.55 (m, 4H), 2.17 (s, 6H), 2.32-2.35 (m, 4H), 3.46 (s, 4H), 5.21 (d, J=10.9 Hz, 2H), 5.73 (d, J=17.6 Hz, 2H), 6.71 (dd, J=17.6, 10.9 Hz, 2H), 7.25 (d, J=8.1 Hz, 2H), 7.35 (d, J=8.1 Hz, 4H).

Copolymerization

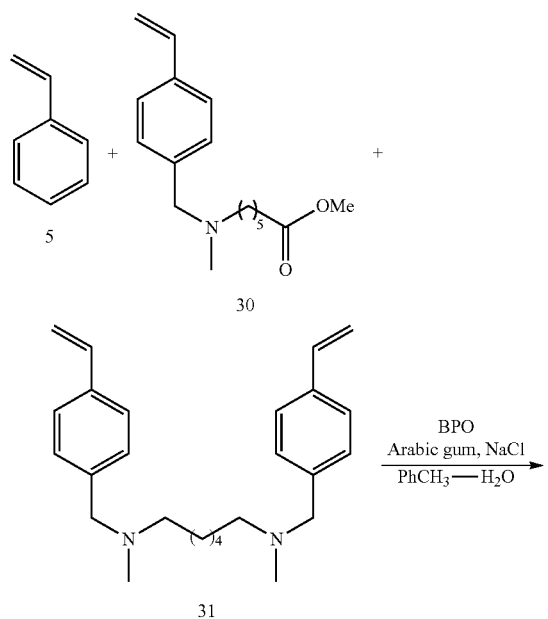

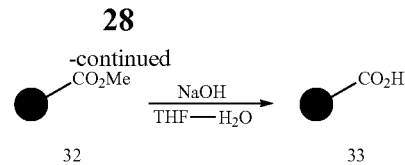

At room temperature, Arabic gum (2.0 g), sodium chloride (5 g) and water (240 mL) are added into a 1000 mL four-neck flask mounted with a mechanical stirrer, nitrogen is blown for 5 hours; a toluene (11.4 g) solution of styrene (5, 10 g, 96 mmol), a monomer (30, 1.11 g, 4.04 mmol), a monomer (31, 376 mg, 1.0 mmol) and BOP (145 mg, 0.6 mmol) is depressurized and degassed for three times by an oil pump, and then added to a violently agitated aqueous phase; a reaction solution is heated to 90° C. and stirred for 24 hours; an obtained white solid is filtered, washed by water (120 mL×2) and methanol (120 mL) respectively, then extracted and washed by THF (120 mL) for 10 hours in a Soxhlet extractor, and dried in vacuum to obtain a polymer 32 (7.7 g, yield 67%), which has an ester group content of 0.352 mmol/g which is calculated according to the proportions of the used monomers.

At room temperature, the polymer 32 (7.7 g, about 2.71 mmol) is suspended in THF (77 mL), and stood for 0.5 hour; then an aqueous (36 mL) solution of sodium hydroxide (2.17 g, 54 mmol) is added, the temperature is increased to 50° C. and stirring is performed for 3 days; filtering is performed, and washing is performed by water, hydrochloric acid with a concentration of 1 mol/L, water, saturated sodium bicarbonate, water and methanol in turn, and drying is performed to obtain a polymer 33 (7.1 g), which has a theoretical carboxyl content of 0.352 mmol/g. The main particle size of the polymer in a dry state is in a range of 150~750 μm.

Measured values of element analysis: C: 90.10%%, H: 7.930%, N: 0.82%, and the calculated O content is 1.150%. Therefore the actual carboxyl content is about 0.359 mmol/g.

Polymer 33, FT-IR (KBr, cm$^{-1}$): 3443, 3025, 2921, 2852, 1601, 1493, 1452, 755, 696. There is no absorption peak around 1800 cm$^{-1}$, which indicates that double bonds have been fully polymerized.

Embodiment 7

Monomer Synthesis

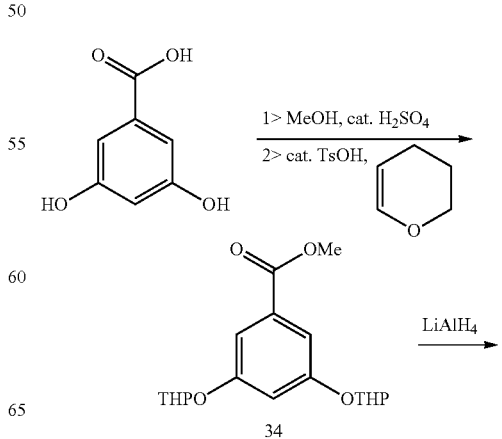

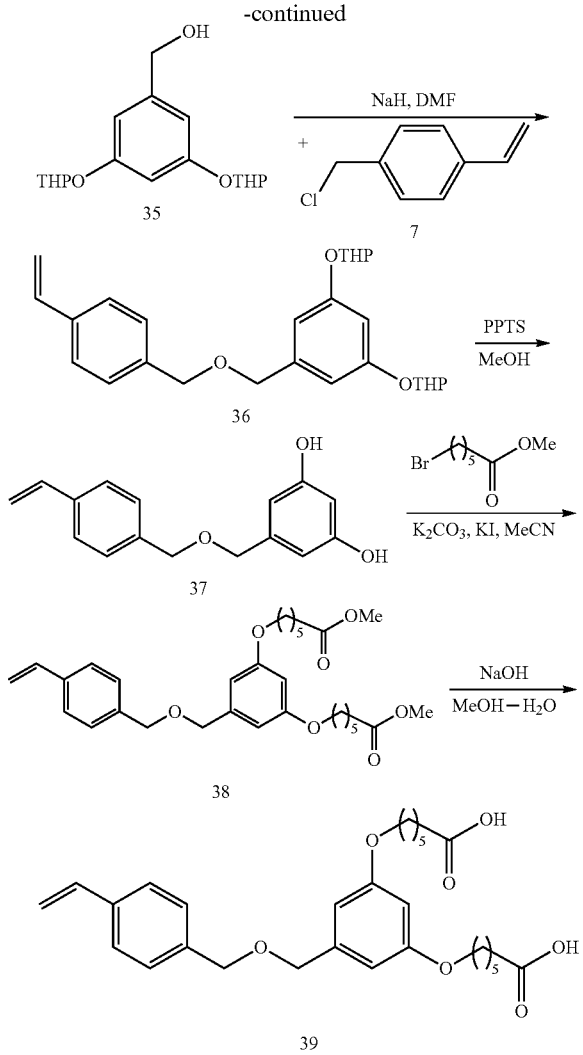

Synthesis of Compound 37

3,5-dihydroxybenzoic acid (50 g, 324.4 mmol) and methanol (500 mL) are added to a reaction flask at room temperature, and then concentrated sulfuric acid (5 g) is added; a mixed solution is heated until a reflux reaction is carried out for 10 hours; a reaction solution is cooled to room temperature, depressurized and concentrated until there is no fraction, dissolved by ethyl acetate, washed by a saturated sodium bicarbonate solution and a saturated brine respectively, then dried by anhydrous sodium sulfate, filtered to remove the drying agent, depressurized and concentrated until there is no fraction; a crude product is added with dichloromethane (750 mL) and p-toluene sulfonic acid monohydrate (3.08 g, 16 mmol), and cooled to 0° C.; dihydropyran (81.8 g, 974 mmol) is dropped; after the dropping, the temperature is recovered to room temperature naturally and a reaction is carried out; after the reaction is carried out completely, the system is quenched by NaHCO₃ with a volume of 10 times; organic phases are separated, washed by a saturated brine with a volume of 5 times, and then dried by anhydrous sodium sulfate; filtering is performed to remove the drying agent, and depressurization and concentration are performed until there is no fraction to obtain a crude product of a compound 34 (98.2 g, yield about 90%), which is directly used in a reaction of the next step.

Lithium aluminum hydride (12.2 g, 321 mmol) and THF (200 mL) are added to a reaction flask at room temperature, and then cooled to 0° C.; a THF (800 mL) solution of the compound 34 (98 g, 292 mmol) is dropped; after the dropping, stirring is performed sequentially for 30 minutes, and then quenching is performed by water (12.2 g), sodium hydroxide (24.4 g) with a concentration of 10% and water (36.6 g); filtering is performed, and a filter cake is washed by THF and concentration is performed to obtain a compound 35 (88.2 g, yield 98%), which is directly used in a reaction of the next step.

NaH (content 60%, 7.05 g, 176 mmol) and DMF (180 mL) are added to a reaction flask at room temperature, and cooled to 0° C.; a DMF (45 mL) solution of the compound 35 (50 g, 162 mmol) is dropped; after the dropping, stirring is performed sequentially for 0.5 hour, and then p-vinylbenzyl chloride (7, 26.8 g, 176 mmol) is dropped; the temperature of a mixed solution is increased to room temperature naturally and stirred for 4 hours; the reaction is quenched by saturated ammonium chloride, and extraction is performed by MTBE; organic phases are combined, washed by a saturated brine, dried by anhydrous sodium sulfate, filtered to remove the drying agent, depressurized and concentrated until there is no fraction to obtain a crude product of a compound 36, which is directly used in a reaction of the next step.

The crude product of the compound 36 and methanol (400 mL) are added to a reaction flask at room temperature, then pyridinium p-toluenesulfonate (4.07 g, 16.2 mmol) is added, and stirring is performed at room temperature for 18 hours; the reaction system is concentrated until there is no fraction, and a crude product is purified by silica gel column chromatography to obtain a compound 37 (35.2 g, yield of two steps 85%).

Compound 37: ¹H NMR (d₆-DMSO, 400 MHz): δ4.35 (s, 2H), 4.47 (s, 2H), 5.25 (d, J=10.9 Hz, 1H), 5.83 (d, J=17.7 Hz, 1H), 6.13 (s, 1H), 6.21 (s, 2H), 6.73 (dd, J=17.6, 10.9 Hz, 1H), 7.32 (d, J=7.8 Hz, 2H), 7.47 (d, J=7.9 Hz, 2H), 9.22 (s, 2H).

Synthesis of Compound 39

The compound 37 (6.0 g, 23.4 mmol), methyl 6-bromohexanoate (10.76 g, 51.5 mmol), potassium carbonate (7.12 g, 51.5 mmol), potassium iodide (777 mg, 4.7 mmol) and acetonitrile (120 mL) are added into a reaction flask at room temperature; a reaction solution is heated until a reflux reaction is carried out for 20 hours; depressurization and filtering are performed to remove a solid, a filtrate is depressurized and concentrated until there is no fraction, and a crude product is purified by silica gel column chromatography to obtain a compound 38 (8.42 g, yield 92%).

The compound 38 (9.72 g, 18.9 mmol) and methanol (50 mL) are added to a reaction flask at room temperature, then an aqueous (20 mL) solution of NaOH (2.27 g, 56.8 mmol) is added; stirring is performed at room temperature for 2 hours, depressurization and concentration are performed to remove most methanol, the remainder is diluted by water and then washed by MTBE; an aqueous phase is regulated to pH≤2 by hydrochloric acid with a concentration of 3N and then extracted by EtOAc; organic phases are combined, and dried by anhydrous sodium sulfate; filtering is performed to remove the drying agent, and depressurization and concentration are performed to obtain a compound 39 (8.42 g, yield 92%).

Compound 39: ¹H NMR (CDCl₃, 400 MHz): δ1.48-1.56 (m, 4H), 1.67-1.75 (m, 4H), 1.75-1.81 (m, 4H), 2.39 (t, J=7.4 Hz, 4H), 3.94 (t, J=6.3 Hz, 4H), 5.24 (d, J=10.9 Hz, 1H), 5.75 (d, J=18.1 Hz, 1H), 6.37 (t, J=2.1 Hz, 1H), 6.49 (d, J=2.1 Hz, 2H), 6.72 (dd, J=17.6, 10.9 Hz, 1H), 7.32 (d, J=8.1 Hz, 2H), 7.40 (d, J=8.1 Hz, 2H).

Copolymerization

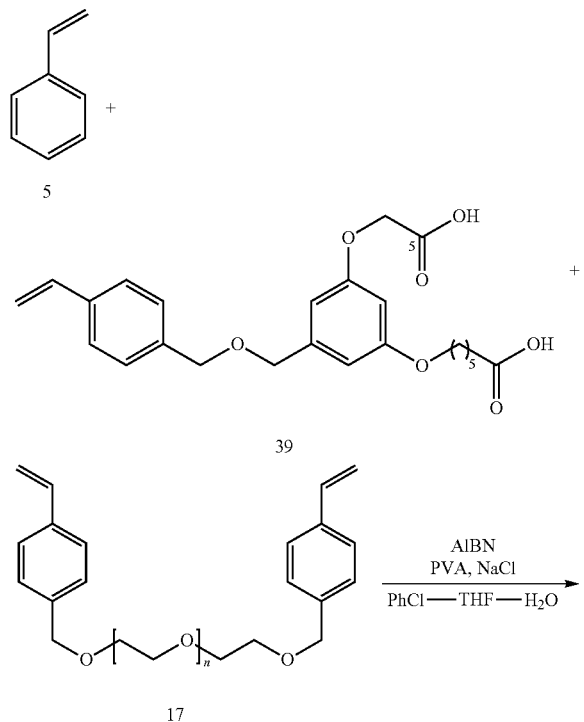

At room temperature, polyvinyl alcohol (2.0 g), sodium chloride (2.0 g) and water (200 mL) are added into a 1000 mL four-neck flask mounted with a mechanical stirrer, heated until being fully dissolved, and cooled to room temperature; nitrogen is blown for 5 hours, a chlorobenzene (10.3 g) and THF (3.4 g) solution of styrene (5, 8 g, 76.8 mmol), a monomer (39, 0.98 g, 2.02 mmol), a monomer (17, prepared in Embodiment 3, 1.28 g, 2.02 mmol) and AIBN (131.4 mg, 0.8 mmol) is depressurized and degassed for three times by an oil pump, and then added to a violently agitated aqueous phase; a reaction solution is heated to 80° C. and stirred for 24 hours; an obtained white solid is filtered, washed by water (120 mL×2) and methanol (120 mL) respectively, then extracted and washed by THF (120 mL) for 16 hours in a Soxhlet extractor, and dried in vacuum to obtain a polymer 40 (7.39 g, yield 72%), which has a theoretical carboxyl content of 0.393 mmol/g. The main particle size of the polymer in a dry state is in a range of 100~900 μm.

The carboxyl content is measured according to the following method:

At room temperature, 1.0 g of the compound 40 is suspended in 40 mL of dichloromethane, and stood for 30~40 minutes; then 2.0 g of benzylamine, 220 mg of 4-dimethylaminopyridine and 1.87 g of triethylamine are added in a stirring condition, 3.56 g of EDCl is added by batches finally, and stirring is performed overnight; the system is subjected to suction filtration, and washed by dichloromethane, THF, methanol, water and methanol in turn; an obtained polymer is further reacted twice in the same conditions, and a finally-obtained polymer is depressurized and dried overnight at 40° C.~50° C.

It is measured by element analysis that the content of each element is as follows: C: 87.23%, H: 7.799% and N: 0.57%; the calculated O content is 4.41%, it is calculated that the molar content of N atoms is 0.407 mmol/g, and it is corrected that the actual carboxyl content is 0.393 mmol/g.

Polymer 40, FT-IR (KBr, cm$^{-1}$): 3420, 3025, 3001, 2921, 1737, 1601, 1493, 1452, 756, 695, 536. There is no absorption peak around 1800 cm$^{-1}$, which indicates that double bonds have been fully polymerized.

Embodiment 8

Monomer Synthesis

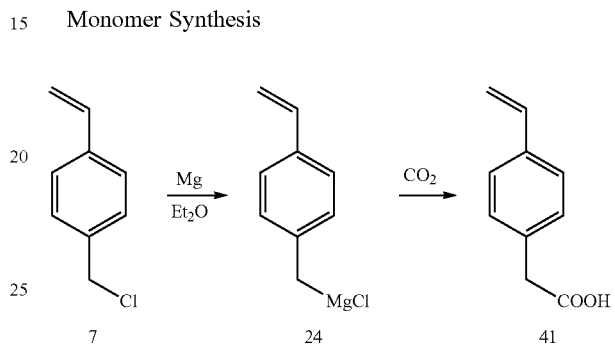

Monomer 41 is prepared with reference to a literature (*Macromolecules*, 2004, 37: 377-384).

Copolymerization

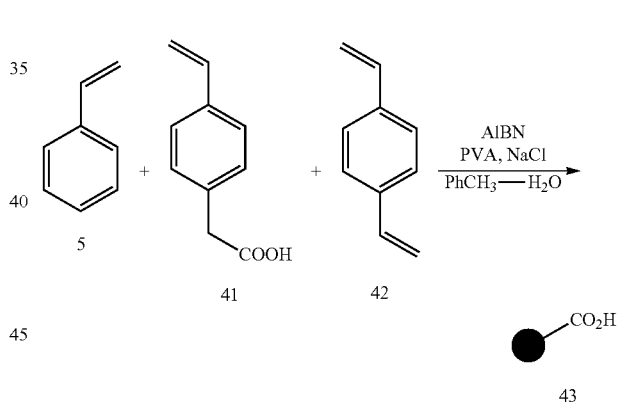

At room temperature, polyvinyl alcohol (0.6 g), sodium chloride (1.2 g) and water (120 mL) are added into a 500 mL four-neck flask mounted with a mechanical stirrer, heated until being fully dissolved, and cooled to room temperature; nitrogen is blown for 5 hours, a toluene (4.8 g) solution of styrene (5, 8 g, 76.8 mmol), a monomer (41, 1.23 g, 6.98 mmol), a monomer (42, content 55%, a mixture of p-divinyl benzene and o-divinyl benzene, 0.83 g, 3.49 mmol) and AIBN (115 mg, 0.7 mmol) is depressurized and degassed for three times by an oil pump, and then added to a violently agitated aqueous phase; a reaction solution is heated to 80° C. and stirred for 24 hours; an obtained white solid is filtered, washed by water (120 mL×2) and methanol (120 mL) respectively, then extracted and washed by THF (120 mL) for 16 hours in a Soxhlet extractor, and dried in vacuum to obtain a polymer 43 (7.36 g, yield 76%), which has a theoretical carboxyl content of 0.721 mmol/g. The main particle size of the polymer in a dry state is in a range of 200~900 μm.

Measured values of element analysis: C: 89.59%, H: 7.577%, and the calculated O content is 2.833%. Therefore the actual carboxyl content is about 0.885 mmol/g.

Polymer 43, FT-IR (KBr, cm$^{-1}$): 3417, 3025, 2921, 2851, 1601, 1493, 1452, 756, 696. There is no absorption peak around 1800 cm$^{-1}$, which indicates that double bonds have been fully polymerized.

Embodiment 9

Monomer Synthesis

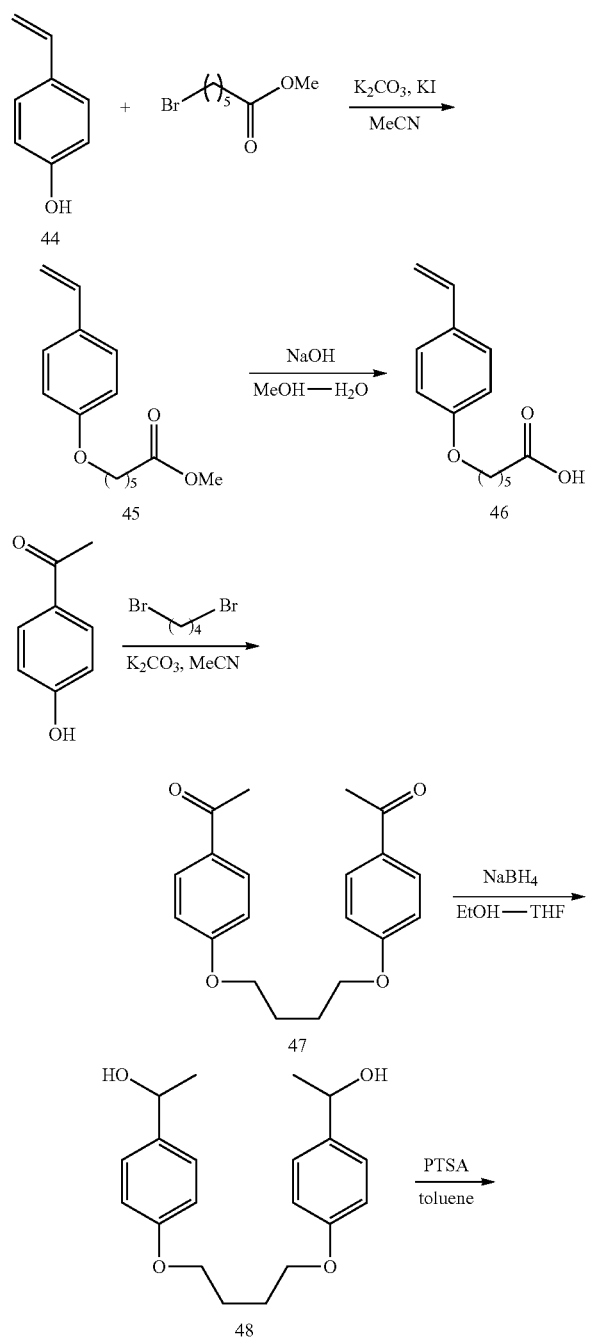

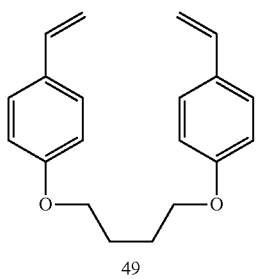

Synthesis of Compound 46

At room temperature, p-hydroxystyrene (44, 5.0 g, 41 mmol), methyl 6-bromohexanoate (10.76 g, 51.5 mmol), potassium carbonate (7.12 g, 51.5 mmol), potassium iodide (690 mg, 0.41 mmol) and acetonitrile (75 mL) are added into a reaction flask; a reaction solution is heated until a reflux reaction is carried out for 20 hours; depressurization and filtering are performed to remove a solid, a filtrate is depressurized and concentrated until there is no fraction, and a crude product is purified by silica gel column chromatography to obtain a compound 45 (8.96 g, yield 88%).

The compound 45 (8.8 g, 35.4 mmol) and methanol (45 mL) are added to a reaction flask at room temperature, then an aqueous (20 mL) solution of NaOH (2.12 g, 53.1 mmol) is added, stirring is performed at room temperature for 1 hour; depressurization and concentration are performed to remove most methanol, the remainder is diluted by water and then washed by MTBE; an aqueous phase is regulated to pH≤2 by hydrochloric acid with a concentration of 3 mol/L and then extracted by EtOAc, organic phases are combined, and dried by anhydrous sodium sulfate; filtering is performed to remove the drying agent, and depressurization and concentration are performed to obtain a compound 46 (7.88 g, yield 95%).

Compound 46: $^1$H NMR (CDCl$_3$, 400 MHz): δ1.29-1.36 (m, 2H), 1.45-1.55 (m, 2H), 1.57-1.69 (m, 2H), 2.37 (t, J=7.4 Hz, 2H), 4.01-4.07 (m, 2H), 5.12 (d, J=10.9 Hz, 1H), 5.61 (d, J=17.6 Hz, 1H), 6.66 (dd, J=17.6, 10.9 Hz, 1H), 6.86 (d, J=8.7 Hz, 2H), 7.35 (d, J=8.7 Hz, 2H).

Synthesis of Compound 49

The compound 49 is synthesized with reference to a literature (*Chemical reagents:* 2006, 28: 1-2).

Copolymerization

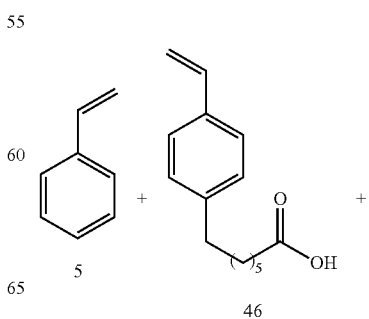

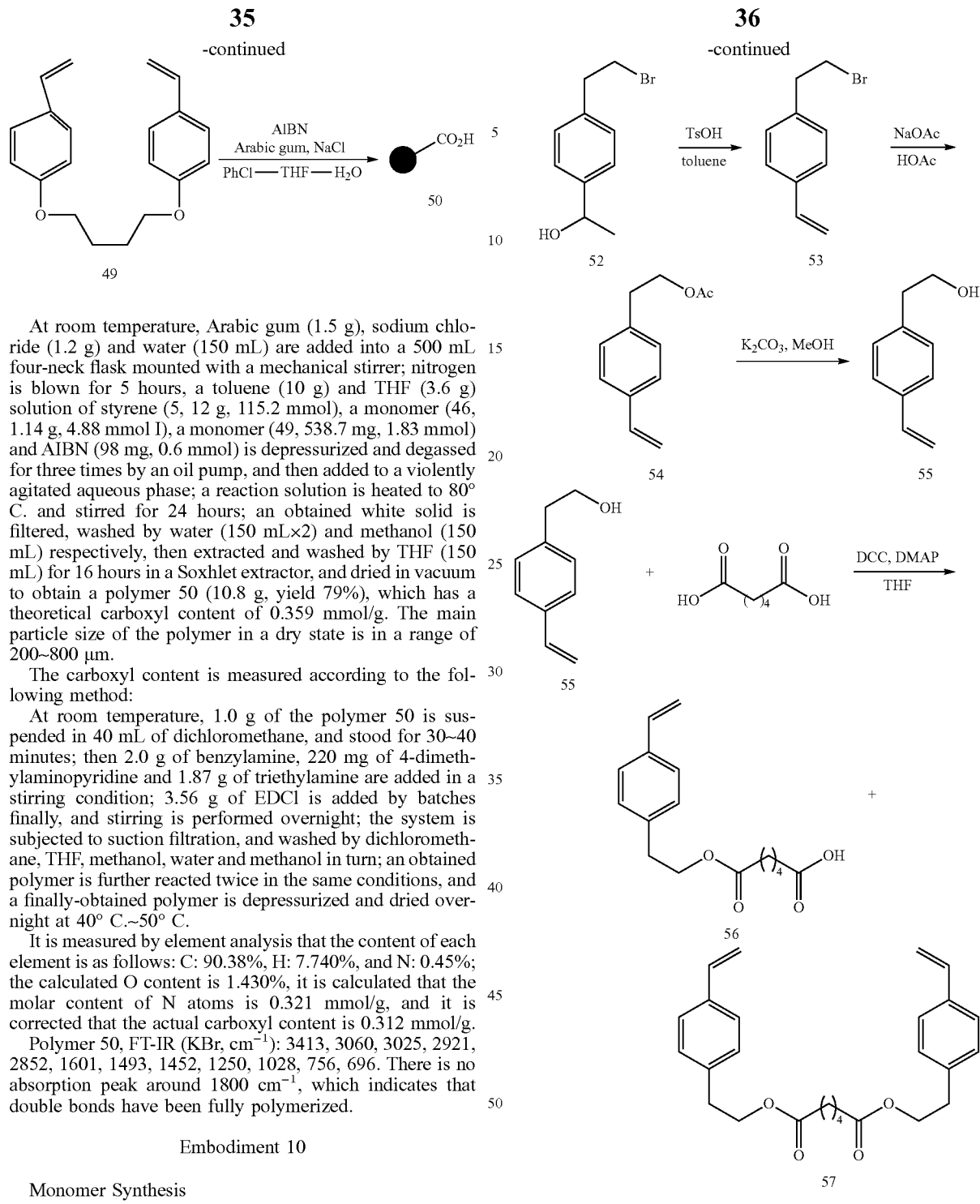

At room temperature, Arabic gum (1.5 g), sodium chloride (1.2 g) and water (150 mL) are added into a 500 mL four-neck flask mounted with a mechanical stirrer; nitrogen is blown for 5 hours, a toluene (10 g) and THF (3.6 g) solution of styrene (5, 12 g, 115.2 mmol), a monomer (46, 1.14 g, 4.88 mmol I), a monomer (49, 538.7 mg, 1.83 mmol) and AIBN (98 mg, 0.6 mmol) is depressurized and degassed for three times by an oil pump, and then added to a violently agitated aqueous phase; a reaction solution is heated to 80° C. and stirred for 24 hours; an obtained white solid is filtered, washed by water (150 mL×2) and methanol (150 mL) respectively, then extracted and washed by THF (150 mL) for 16 hours in a Soxhlet extractor, and dried in vacuum to obtain a polymer 50 (10.8 g, yield 79%), which has a theoretical carboxyl content of 0.359 mmol/g. The main particle size of the polymer in a dry state is in a range of 200~800 μm.

The carboxyl content is measured according to the following method:

At room temperature, 1.0 g of the polymer 50 is suspended in 40 mL of dichloromethane, and stood for 30~40 minutes; then 2.0 g of benzylamine, 220 mg of 4-dimethylaminopyridine and 1.87 g of triethylamine are added in a stirring condition; 3.56 g of EDCl is added by batches finally, and stirring is performed overnight; the system is subjected to suction filtration, and washed by dichloromethane, THF, methanol, water and methanol in turn; an obtained polymer is further reacted twice in the same conditions, and a finally-obtained polymer is depressurized and dried overnight at 40° C.~50° C.

It is measured by element analysis that the content of each element is as follows: C: 90.38%, H: 7.740%, and N: 0.45%; the calculated O content is 1.430%, it is calculated that the molar content of N atoms is 0.321 mmol/g, and it is corrected that the actual carboxyl content is 0.312 mmol/g.

Polymer 50, FT-IR (KBr, cm$^{-1}$): 3413, 3060, 3025, 2921, 2852, 1601, 1493, 1452, 1250, 1028, 756, 696. There is no absorption peak around 1800 cm$^{-1}$, which indicates that double bonds have been fully polymerized.

Embodiment 10

Monomer Synthesis

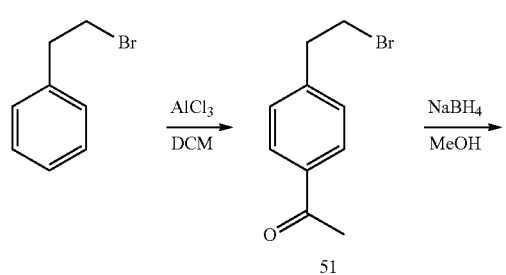

Synthesis of Compound 53

At room temperature, anhydrous aluminium chloride (400 g, 3 mol) and dichloromethane (1.5 L) are added into a reaction flask, and cooled to 0° C.; a dichloromethane (500 mL) solution of acetyl chloride (234.7 g, 3 mol) is dropped, and then a dichloromethane (500 mL) solution of β-bromoethylbenzene (500 g, 2.72 mmol) is dropped; the reaction system is stirred sequentially at 0° C. for 3 hours, and poured into ice water to perform quenching; solutions are separated, and organic phases are extracted by dichloromethane; the organic phases are combined, washed by a saturated brine, depressurized and concentrated to obtain a crude product (567 g, yield 92%) of a compound 51, which is directly used in a reaction of the next step. It is shown by a liquid phase that the ratio of para-isomerides to ortho-isomers is 8.2:1.

The crude product (550 g, 2.42 mol) of the compound 51 and methanol (2.8 mL) are added to a reaction flask at room temperature, and cooled to 0° C.; sodium borohydride (36.7 g, 0.97 mol) is added by batches; the reaction system is stirred sequentially at 0° C. for 5 hours, poured into saturated ammonium chloride to quench a reaction; and then extracted by ethyl acetate; organic phases are combined, washed by a saturated brine, depressurized and concentrated to obtain a crude product (555 g, yield 100%) of a compound 52, which is directly used in a reaction of the next step.

The crude product (550 g, 2.42 mol) of the compound 52 and methanol (8.2 L) are added to a reaction flask at room temperature, p-toluene sulfonic acid monohydrate (11.4 g, 6.0 mmol) is added; heating is performed until refluxing happens, water generated by the system is separated by a water separator; after a reaction is carried out completely, the temperature is reduced to room temperature, washing is performed with saturated sodium bicarbonate and a saturated brine, filtering is performed by a layer of silica gel, and then concentration is performed until there is no fraction; a crude product is subjected to reduced pressure distillation to obtain a compound 53 (460 g, yield 90%) and it is shown by MNR that the ratio of para-isomerides to ortho-isomers is 7.7:1.

Compound 53: $^1$H NMR (CDCl$_3$, 400 MHz): δ3.17 (t, J=7.6 Hz, 1H), 3.58 (t, J=7.6 Hz, 1H), 5.26 (d, J=10.9 Hz, 1H), 5.76 (d, J=17.6 Hz, 1H), 6.73 (dd, J=17.6, 10.9 Hz, 1H), 7.20 (d, J=8.0 Hz, 1H), 7.40 (d, J=8.0 Hz, 1H).

Synthesis of Compound 55

At room temperature, the compound 53 (80 g, 379 mmol) and acetic acid (240 mL) are added to a reaction flask, then anhydrous sodium acetate (74.4 g, 758 mmol) is added, heating and refluxing are performed for 24 hours; the temperature is reduced to room temperature, the system is slowly dropped into a saturated sodium bicarbonate solution cooled by an ice-water bath, and then extracted by ethyl acetate; organic phases are combined, washed by a saturated brine, and then concentrated until there is no fraction to obtain a crude product (72.4 g) of a compound 54, which is directly used in a reaction of the next step.

The crude product of the compound 54 (72.4 g) obtained in the last step and methanol (500 mL) are added into a reaction flask at room temperature, then potassium carbonate (105 g, 757 mmol) is added, stirring is performed for 2 hours; the reaction system is concentrated until there is no fraction, MTBE and water are added to perform solution separation, an aqueous phase is further extracted by MTBE; organic phases are combined, washed by a saturated brine, and then concentrated until there is no fraction, and a crude product is purified by silica gel column chromatography to obtain a compound 55 (46.5 g, yield 83%).

Compound 55: $^1$H NMR (CDCl$_3$, 400 MHz): δ 1.96 (brs, 1H), 2.85 (t, J=6.5 Hz, 1H), 3.83 (t, J=6.5 Hz, 1H), 5.24 (d, J=10.9 Hz, 1H), 5.74 (d, J=17.6 Hz, 1H), 6.72 (dd, J=17.6, 10.9 Hz, 1H), 7.20 (d, J=8.1 Hz, 2H), 7.38 (d, J=8.1 Hz, 2H).

Synthesis of Compounds 56 and 57

At room temperature, dicyclohexylcarbodiimide (30.4 g, 148 mmol) is added into a THF (300 mL) solution of the compound 55 (20 g, 135 mmol), adipic acid (18.1 g, 135 mmol) and 4-dimethylaminopyridine (1.65 g, 13.5 mmol) by batches; stirring is performed sequentially for 4 hours at room temperature, filtering is performed to remove an insoluble substance; the remainder is dissolved with ethyl acetate (300 mL), washed by hydrochloric acid (100 mL×2) with a concentration of 1N, dried by anhydrous sodium sulfate and then concentrated until there is no fraction, and the remainder are purified by silica gel column chromatography to obtain a compound 56 (14.9 g, yield 40%) and a compound 57 (11.2 g, yield 41%).

Compound 56: $^1$H NMR (CDCl$_3$, 400 MHz): δ1.66-1.70 (m, 4H), 2.35-2.41 (m, 4H), 2.83 (t, J=6.5 Hz, 2H), 4.41 (t, J=6.5 Hz, 2H), 5.26 (d, J=10.9 Hz, 1H), 5.75 (d, J=17.6 Hz, 1H), 6.72 (dd, J=17.6, 10.9 Hz, 1H), 7.20 (d, J=8.1 Hz, 2H), 7.37 (d, J=8.1 Hz, 2H).

Compound 57: $^1$H NMR (CDCl$_3$, 400 MHz): δ1.65-1.70 (m, 4H), 2.34-2.39 (m, 4H), 2.83 (t, J=6.6 Hz, 4H), 4.42 (t, J=6.5 Hz, 4H), 5.24 (d, J=10.9 Hz, 2H), 5.74 (d, J=17.6 Hz, 2H), 6.72 (dd, J=17.6, 10.9 Hz, 2H), 7.18 (d, J=8.0 Hz, 4H), 7.36 (d, J=8.0 Hz, 4H).

Copolymerization

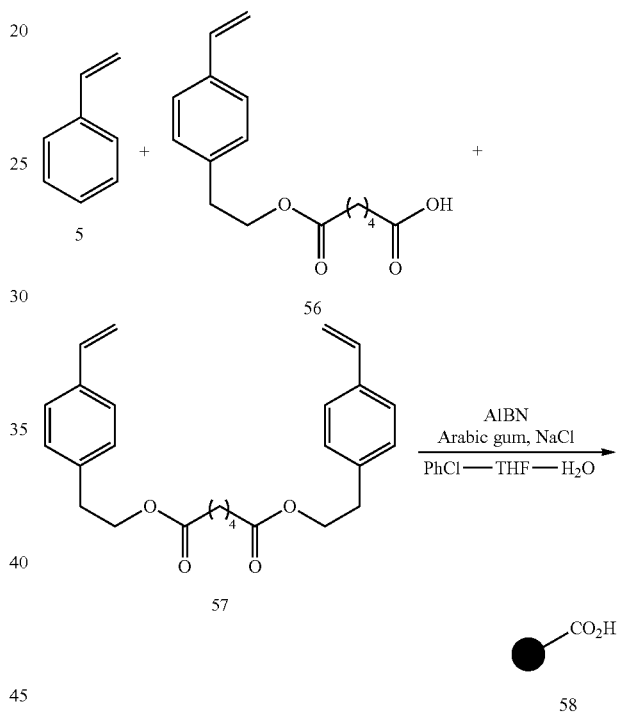

At room temperature, Arabic gum (4 g), sodium chloride (8 g) and water (300 mL) are added into a 1000 mL four-neck flask mounted with a mechanical stirrer; nitrogen is blown for 5 hours, a chlorobenzene (63 g) and THF (14 g) solution of styrene (5, 30 g, 288 mmol), a monomer (56, 3.83 g, 13.86 mmol), a monomer (57, 2.5 g, 6.16 mmol) and AIBN (303 mg, 1.85 mmol) is depressurized and degassed for three times by an oil pump, and then added to a violently agitated aqueous phase; a reaction solution is heated to 80° C. and stirred for 24 hours; an obtained white solid is filtered, washed by water (400 mL×2) and methanol (400 mL) respectively, then extracted and washed by THF (400 mL) for 16 hours in a Soxhlet extractor, and dried in vacuum to obtain a polymer 58 (29.8 g, yield 82%), which has a theoretical carboxyl content of 0.381 mmol/g. The main particle size of the polymer in a dry state is in a range of 200~900 μm.

The carboxyl content is measured according to the same method as that in Embodiment 1 and the carboxyl content is about 0.331 mmol/g.

Polymer 58, FT-IR (KBr, cm$^{-1}$): 3420, 3025, 2921, 2852, 1704, 1601, 1493, 1452, 757, 694. There is no absorption peak around 1800 cm$^{-1}$, which indicates that double bonds have been fully polymerized.

Embodiment 11

Copolymerization

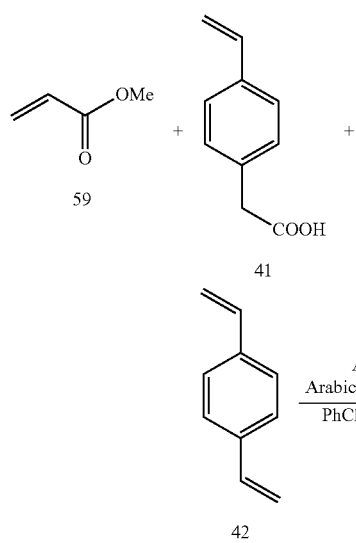

At room temperature, Arabic gum (0.9 g), sodium chloride (1.8 g) and water (90 mL) are added into a 500 mL four-neck flask mounted with a mechanical stirrer; nitrogen is blown for 5 hours; a chlorobenzene (18 g) solution of methacrylate (5.15 g, 174 mmol), a monomer (41, prepared in Embodiment 8, 1.88 g, 13.86 mmol), a monomer (42, content 55%, a mixture of o-divinylbenzene and p-divinylbenzene, 2.28 g, 11.6 mmol) and AIBN (196 mg, 1.2 mmol) is depressurized and degassed for three times by an oil pump, and then added to a violently agitated aqueous phase; a reaction solution is heated to 80° C. and stirred for 24 hours; an obtained white solid is filtered, washed by water (250 mL×2) and methanol (250 mL) respectively, then extracted and washed by THF (250 mL) for 16 hours in a Soxhlet extractor, and dried in vacuum to obtain a polymer 60 (14.5 g, yield 80%), which has a theoretical carboxyl content of 0.764 mmol/g. The main particle size of the polymer in a dry state is in a range of 200~900 μm.

Polymer 60, FT-IR (KBr, cm$^{-1}$): 3414, 3025, 2921, 2852, 1737, 1715, 1601, 1493, 1452, 757, 696, 534. There is no absorption peak around 1800 cm$^{-1}$, which indicates that double bonds have been fully polymerized.

Supported metal catalysts are prepared in Embodiment 12 to 18 using the polymers above as carriers, and penem antibiotic intermediates are prepared by the supported metal catalysts through carbene reactions.

Embodiment 12

Rhodium Exchange Reaction

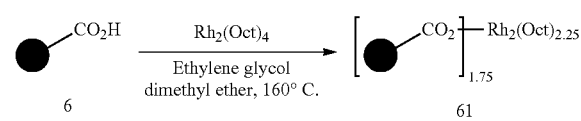

The polymer 6 (1.0 g, 0.358 mmol-CO$_2$H/g, prepared in Embodiment 1), rhodium octanoate (557 mg, 0.716 mmol) and diethylene glycol dimethyl ether (20 mL) are added to a reaction flask and heated to 160° C.; 1 hour later, a reaction mixture is cooled to room temperature, THF (20 mL) is added, and stirring is performed for 10 minutes; filtering is performed, and a polymer is washed by THF until a filtrate is colorless; the filtrate is collected so as to recover unreacted rhodium octanoate; an obtained polymer is washed by dichloromethane (20 mL) and ethyl acetate (20 mL) sequentially, and then depressurized and dried to obtain a dark green rhodium catalyst 61. It is measured by an Inductively Coupled Plasma (ICP) spectrum instrument that the rhodium content is 38190 ppm (0.37 mmol/g).

Catalyst 61, FT-IR (KBr, cm$^{-1}$): 3417, 3060, 3025, 2922, 2850, 1735, 1601, 1578, 1492, 1452, 1413, 1153, 754, 695.

Carbene Insertion Reaction

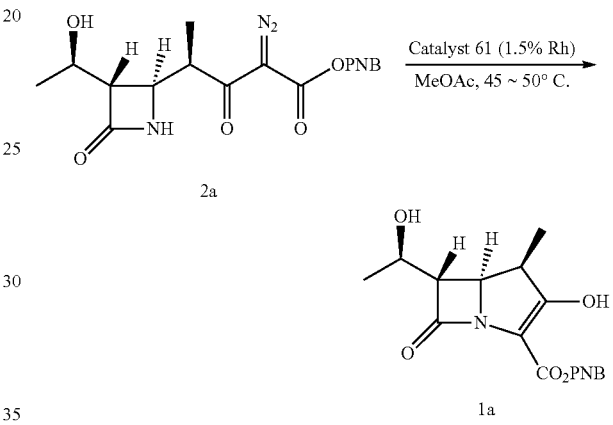

The catalyst 61 (324 mg, 0.12 mmol Rh) and methyl acetate (24 mL) are added into a reaction flask, and swelling is performed for 0.5 hour at room temperature; a compound 2a (3.0 g, 7.7 mmol) is added at a time, and then a reaction mixture is heated to 45° C.~50° C. to react; after the reaction, the reaction mixture is cooled to room temperature, filtered to remove the catalyst 61, and washed by methyl acetate (3 mL×2); combined organic phases containing a compound 1a are directly used in a phosphate esterification of the next step. The High Performance Liquid Chromatography (HPLC) external standard yield is 99.6% (using a reaction with rhodium octanoate has a catalyst for reference), and the loss of rhodium is smaller than 0.6%.

Embodiment 13

Rhodium Exchange Reaction

The polymer 11 (1.0 g, 0.365 mmol-CO$_2$H/g, prepared in Embodiment 2), rhodium octanoate (568 mg, 0.716 mmol) and toluene (20 mL) are added to a reaction flask and heated to reflux; 12 hours later, a reaction mixture is cooled to room temperature, THF (20 mL) is added, and stirring is performed for 10 minutes; filtering is performed, and a polymer is washed by THF until a filtrate is colorless; the filtrate is collected so as to recover unreacted rhodium octanoate; an obtained polymer is washed by dichloromethane (20 mL) and ethyl acetate (20 mL) sequentially, and then depressurized and dried to obtain a dark green rhodium catalyst 62. It is measured by ICP that the rhodium content is 32390 ppm (0.31 mmol/g).

Catalyst 62, FT-IR (KBr, cm$^{-1}$): 3419, 3025, 2923, 2850, 1735, 1618, 1523, 1492, 1130, 695.

Carbene Insertion Reaction

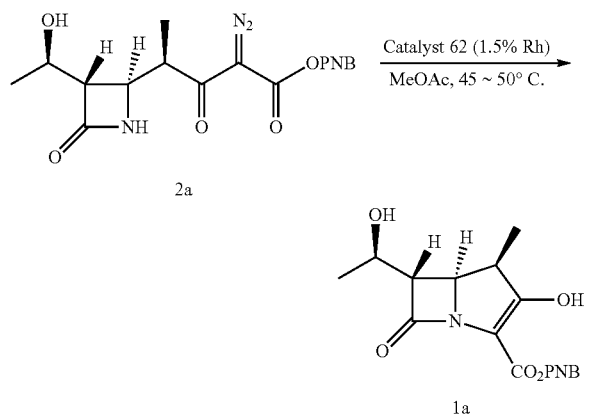

2a

1a

The catalyst 62 (448 mg, 0.12 mmol Rh) and methyl acetate (24 mL) are added into a reaction flask, and swelling is performed for 0.5 hour at room temperature; a compound 2a (3.0 g, 7.7 mmol) is added at a time, and then a reaction mixture is heated to 45° C.~50° C. to react; after the reaction, the reaction mixture is cooled to room temperature, filtered to remove the catalyst 62, and washed by methyl acetate (3 mL×2); combined organic phases containing a compound 1a are directly used in a phosphate esterification of the next step. The HPLC external standard yield is 98.2% (using a reaction with rhodium octanoate has a catalyst for reference), and the loss of rhodium is smaller than 1.0%.

Embodiment 14

Rhodium Exchange Reaction

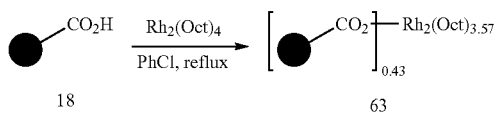

18                                63

The polymer 18 (1.0 g, 0.433 mmol-CO$_2$H/g, prepared in Embodiment 3), rhodium octanoate (628 mg, 0.808 mmol) and chlorobenzene (20 mL) are added to a reaction flask and heated to reflux; 2 hours later, a reaction mixture is cooled to room temperature, THF (20 mL) is added, and stirring is performed for 10 minutes; filtering is performed, and a polymer is washed by THF until a filtrate is colorless; the filtrate is collected so as to recover unreacted rhodium octanoate; an obtained polymer is washed by dichloromethane (20 mL) and ethyl acetate (20 mL) sequentially, and then depressurized and dried to obtain a dark green rhodium catalyst 63. It is measured by ICP that the rhodium content is 37730 ppm (0.37 mmol/g).

Catalyst 63, FT-IR (KBr, cm$^{-1}$): 3417, 3025, 2920, 2851, 1601, 1608, 1493, 1452, 1102, 756, 695.

Carbene Insertion Reaction

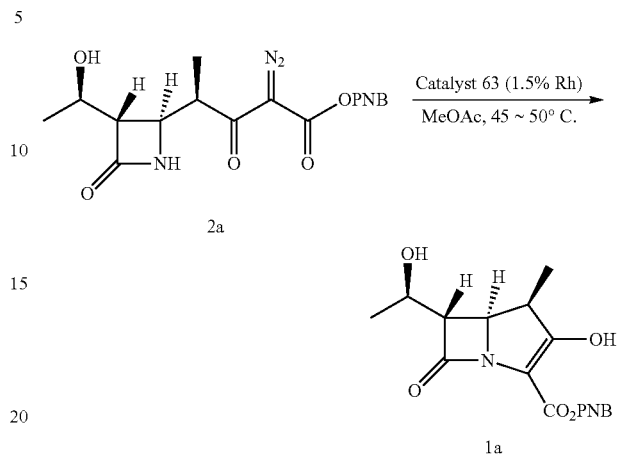

2a

1a

The catalyst 63 (327 mg, 0.12 mmol Rh) and methyl acetate (24 mL) are added into a reaction flask, and swelling is performed for 0.5 hour at room temperature; a compound 2a (3.0 g, 7.7 mmol) is added at a time, and then a reaction mixture is heated to 45° C.~50° C. to react; after the reaction, the reaction mixture is cooled to room temperature, filtered to remove the catalyst 63, and washed by methyl acetate (3 mL×2); combined organic phases containing a compound 1a are directly used in a phosphate esterification of the next step. The HPLC external standard yield is 100.2% (using a reaction with rhodium octanoate has a catalyst for reference), and the loss of rhodium is smaller than 0.6%.

Embodiment 15

Rhodium Exchange Reaction

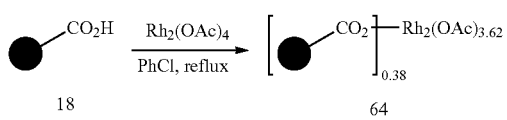

18                                64

The polymer 18 (1.0 g, 0.433 mmol-CO$_2$H/g, prepared in Embodiment 3), rhodium acetate (182 mg, 0.650 mmol) and chlorobenzene (20 mL) are added to a reaction flask and heated to reflux; 2 hours later, a reaction mixture is cooled to room temperature, THF (20 mL) is added, and stirring is performed for 10 minutes; filtering is performed, and a polymer is washed by THF until a filtrate is colorless; the filtrate is collected so as to recover unreacted rhodium acetate; an obtained polymer is washed by dichloromethane (20 mL) and ethyl acetate (20 mL) sequentially, and then depressurized and dried to obtain a dark green rhodium catalyst 64. It is measured by ICP that the rhodium content is 34240 ppm (0.33 mmol/g).

Catalyst 64, FT-IR (KBr, cm$^{-1}$): 3419, 3024, 2921, 2851, 1601, 1493, 1451, 1130, 754, 695.

Carbene Insertion Reaction

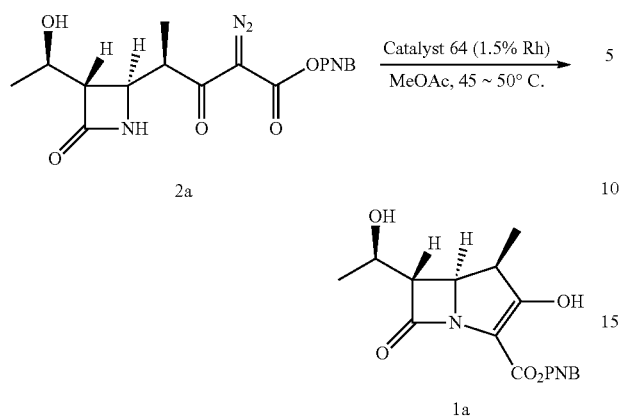

The catalyst 64 (353 mg, 0.12 mmol Rh) and methyl acetate (24 mL) are added into a reaction flask, and swelling is performed for 0.5 hour at room temperature; a compound 2a (3.0 g, 7.7 mmol) is added at a time, and then a reaction mixture is heated to 45° C.~50° C. to react; after the reaction, the reaction mixture is cooled to room temperature, filtered to remove the catalyst 64, and washed by methyl acetate (3 mL×2); combined organic phases containing a compound 1a are directly used in a phosphate esterification of the next step. The HPLC external standard yield is 95.2% (using a reaction with rhodium octanoate has a catalyst for reference), and the loss of rhodium is smaller than 1.0%.

Embodiment 16

Carbene Insertion Reaction

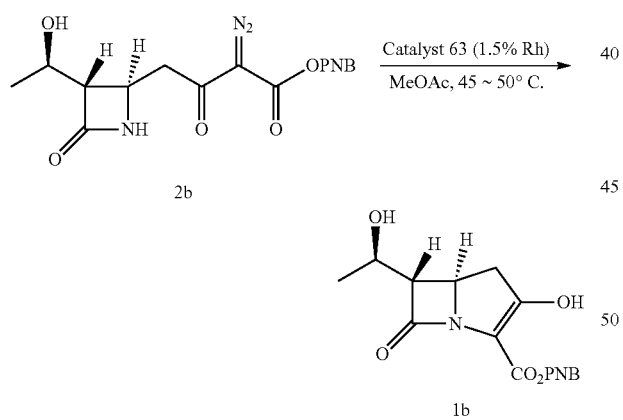

The catalyst 63 (540 mg, 0.2 mmol Rh) and methyl acetate (40 mL) are added into a reaction flask, and swelling is performed for 0.5 hour at room temperature; a compound 2b (5.0 g, 13.3 mmol) is added at a time, and then a reaction mixture is heated to 45° C.~50° C. to react; after the reaction, the reaction mixture is cooled to room temperature, filtered to remove the catalyst 63, and washed by methyl acetate (5 mL×2); combined organic phases containing a compound 1 b are directly used in a phosphate esterification of the next step. The HPLC external standard yield is 96.4% (using a reaction with rhodium octanoate has a catalyst for reference), and the loss of rhodium is smaller than 0.8%.

Embodiment 17

Carbene Insertion Reaction

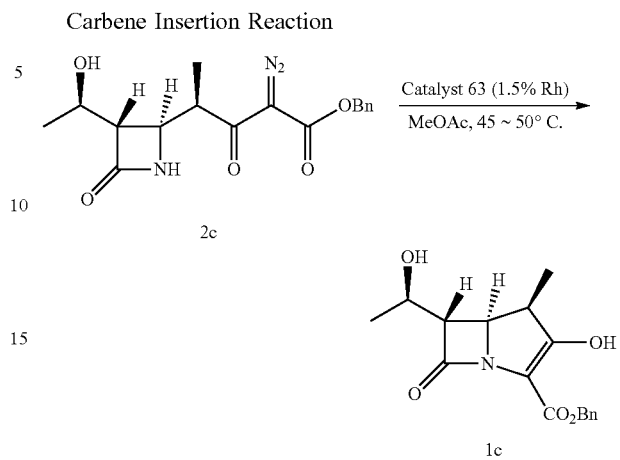

The catalyst 63 (540 mg, 0.2 mmol Rh) and methyl acetate (24 mL) are added into a reaction flask, and swelling is performed for 0.5 hour at room temperature; a compound 2c (5.0 g, 14.5 mmol) is added at a time, and then a reaction mixture is heated to 45° C.~50° C. to react; after the reaction, the reaction mixture is cooled to room temperature, filtered to remove the catalyst 63, and washed by methyl acetate (5 mL×2); combined organic phases containing a compound 1c are directly used in a phosphate esterification of the next step. The HPLC external standard yield is 96.4% (using a reaction with rhodium octanoate has a catalyst for reference), and the loss of rhodium is smaller than 0.8%.

Embodiment 18

Carbene Insertion Reaction

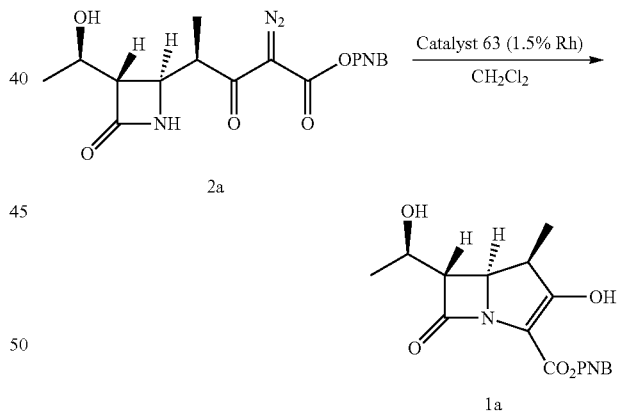

The catalyst 63 (540 mg, 0.2 mmol Rh) and dichloromethane (40 mL) are added into a reaction flask, and swelling is performed for 0.5 hour at room temperature; a compound 2a (5.0 g, 14.5 mmol) is added at a time, and then a reaction mixture is heated to have a reflux reaction; after the reaction, the reaction mixture is cooled to room temperature, filtered to remove the catalyst 63, and washed by dichloromethane (5 mL×2); combined organic phases containing a compound 1a are directly used in a phosphate esterification of the next step. The HPLC external standard yield is 97.4% (using a reaction with rhodium octanoate has a catalyst for reference), and the loss of rhodium is smaller than 0.5%.

Embodiment 19 to 21 is batch reaction tests or continuous mobile phase reactions.

Embodiment 19

Recovery and Recycling of Rhodium Catalyst in Batch Reactions

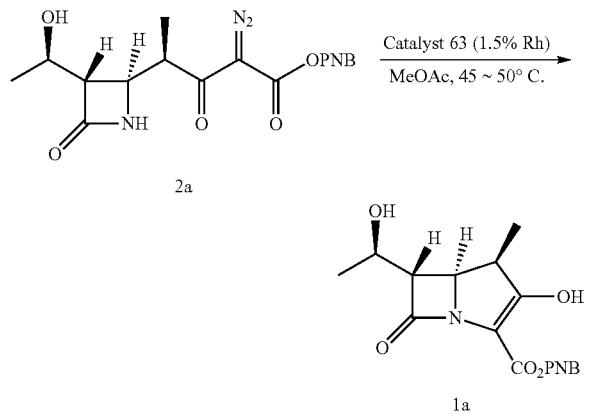

The catalyst 63 (327 mg, 0.12 mmol Rh) and methyl acetate (24 mL) are added to a reaction flask, swelling is performed at room temperature for 0.5 hour; a compound 2a (3.0 g, 7.7 mmol) is added at a time, then a reaction mixture is heated to 45° C.~50° C. to react, the reaction mixture is cooled to room temperature after the reaction is completed, filtering is performed to recover the catalyst 63, and then the catalyst 63 is washed by methyl acetate (5 mL×2) and used directly in the next cycle. The supported catalyst 63 may be used for more than 20 times without evident reduction in the reaction yield. A reaction result is as shown in Table 1.

TABLE 1

| Reaction times | 1 | 6 | 11 | 20 |
|---|---|---|---|---|
| Reaction time/h | 1.0 | 1.5 | 2.0 | 5.0 |
| HPLC external standard yield/% (using a reaction with rhodium octanoate as a catalyst for reference) | 100.2 | 99.6 | 100.0 | 98.9 |

Embodiment 20

Continuous Mobile Phase Reaction Catalyzed by a Supported Rhodium Catalyst

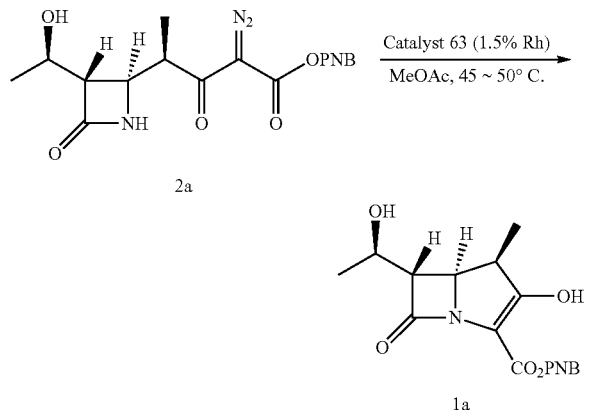

The catalyst 63 (1.1 g, 0.42 mmol Rh, about 5 mL) and methyl acetate (50 mL) are added to a reaction flask, swelling is performed at room temperature for 1 hour; 20 mL of a spiral fiberglass filler is added in the system, and uniformly stirred; then the system is loaded into a tubular reactor by a wet method, and the temperature of a jacket is controlled at 55° C.; 15.0 g of 2a (38.4 mmol) is dissolved in 120 mL of methyl acetate, stirring is performed at room temperature until a homogeneous phase is obtained, and the homogeneous phase is pumped into the tubular reactor at a flow rate of 2.0 mL/min by a plunger pump; a reception bottle is mounted behind the reaction tube to receive a system after a reaction; a received liquid is subjected to representation after material ramming is performed, and a result shows that an HPLC external yield is 99.0% (using a reaction with rhodium octanoate as a catalyst for reference), and loss of rhodium is smaller than 0.6%.

Embodiment 21

Continuous Mobile Phase Reaction Catalyzed by a Supported Rhodium Catalyst

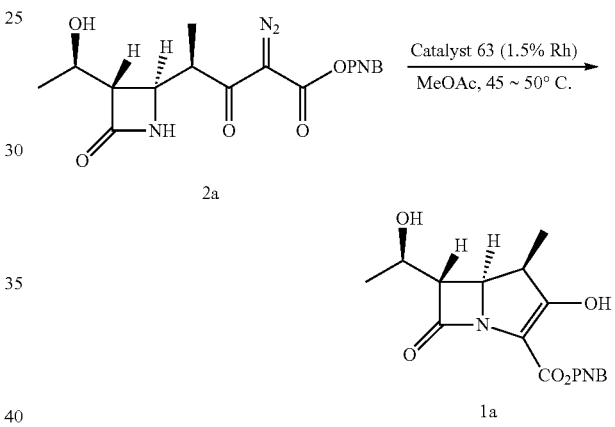

The catalyst 63 (1.1 g, 0.42 mmol Rh, about 5 mL) and methyl acetate (50 mL) are added to a reaction flask, swelling is performed at room temperature for 1 hour; 20 mL of a spiral fiberglass filler is added in the system, and uniformly stirred; then the system is loaded into a tubular reactor by a wet method, the temperature of a jacket is controlled at 45° C.; 215 g of 2a (550.8 mmol) is dissolved in 1.7 L of methyl acetate, stirring is performed at room temperature until a homogeneous phase is obtained, and the homogeneous phase is pumped into the tubular reactor at a flow rate of 0.8 mL/min by a plunger pump; a reception bottle is mounted behind the reaction tube to receive a system after a reaction; samples are analyzed at different time after material ramming is performed, and a result is as shown in Table 2. There is no evident reduction in the reaction yield after 215 g of raw materials are processed continuously in the reaction.

TABLE 2

| Reaction time/h | 0.5 | 15.0 | 35.0 |
|---|---|---|---|
| HPLC external standard yield/% (using a reaction with rhodium octanoate as a catalyst for reference) | 98.9 | 99.5 | 100.0 |

Polymers containing a carboxyl group are prepared in Embodiment 22 to 27 by three monomers of the same types but different molar content, and supported metal catalysts and penem antibiotic intermediates are prepared (methods for synthesizing monomers in Embodiment 22 to 28 are the same as those in Embodiment 1).

Embodiment 22

Copolymerization:
an operation method and technical conditions of copolymerization are the same as those in Embodiment 1, and what is different is the use amount of each monomer, specific use amounts of the monomers are as follows: styrene (5, 24.7 g, 237.4 mmol), a monomer (3, 62 g, 178.8 mmol) and a monomer (4, 82.7 g, 178.8 mmol).
Rhodium Exchange Reaction:
a polymer obtained in the copolymerization is used as a carrier to prepare a supported rhodium catalyst, and a specific preparation process is the same as that in Embodiment 12 except that an organic acid salt of rhodium is rhodium 2-dodecyl decanoate.
Carbene Insertion Reaction:
the supported rhodium catalyst prepared in the rhodium exchange reaction is used as a catalyst to prepare a penem antibiotic intermediate, and the specific raw materials and process are same as those in Embodiment 12.

Embodiment 23

Copolymerization:
an operation method and technical conditions of copolymerization are the same as those in Embodiment 1, and what is different is the use amount of each monomer, specific use amounts of the monomers are as follows: styrene (5, 29.6 g, 284.9 mmol), a monomer (3, 51.7 g, 149 mmol) and a monomer (4, 68.9 g, 149 mmol).
Rhodium Exchange Reaction:
a polymer obtained in the copolymerization is used as a carrier to prepare a supported rhodium catalyst, and a specific preparation process is the same as that in Embodiment 12 except that an applied organic acid salt of rhodium is rhodium pivalate.
Carbene Insertion Reaction:
the supported rhodium catalyst prepared in the rhodium exchange reaction is used as a catalyst to prepare a penem antibiotic intermediate, and the specific raw materials and process are same as those in Embodiment 12 except the use amount of the catalyst. Based on Rh, the use amount of the supported rhodium catalyst is 0.19 mmol.

Embodiment 24

Copolymerization:
an operation method and technical conditions of copolymerization are the same as those in Embodiment 1, and what is different is the use amount of each monomer, specific use amounts of the monomers are as follows: styrene (5, 61 g, 587.6 mmol), a monomer (3, 1 g, 3 mmol) and a monomer (4, 1.4 g, 3 mmol).
Rhodium Exchange Reaction:
a polymer obtained in the copolymerization is used as a carrier to prepare a supported rhodium catalyst, and a specific preparation process is the same as that in Embodiment 12 except that an applied organic acid salt of rhodium is rhodium acetate.
Carbene Insertion Reaction:
the supported rhodium catalyst prepared in the rhodium exchange reaction is used as a catalyst to prepare a penem antibiotic intermediate, and the specific raw materials and process are same as those in Embodiment 12 except the use amount of the catalyst. Based on Rh, the use amount of the supported rhodium catalyst is 0.0048 mmol.

Embodiment 25

Copolymerization:
an operation method and technical conditions of copolymerization are the same as those in Embodiment 1, and what is different is the use amount of each monomer, specific use amounts of the monomers are as follows: styrene (5, 49.4 g, 474.8 mmol), a monomer (3, 21 g, 59.6 mmol) and a monomer (4, 27.6 g, 59.6 mmol).
Rhodium Exchange Reaction:
a polymer obtained in the copolymerization is used as a carrier to prepare a supported rhodium catalyst, and a specific preparation process is the same as that in Embodiment 12 except that an applied organic acid salt of rhodium is rhodium acetate.
Carbene Insertion Reaction:
the supported rhodium catalyst prepared in the rhodium exchange reaction is used as a catalyst to prepare a penem antibiotic intermediate, and the specific raw materials and process are same as those in Embodiment 12 except the use amount of the catalyst. Based on Rh, the use amount of the supported rhodium catalyst is 0.2 mmol.

Embodiment 26

Copolymerization:
an operation method and technical conditions of copolymerization are the same as those in Embodiment 1, and what is different is the use amount of each monomer, specific use amounts of the monomers are as follows: styrene (5, 55.6 g, 534.2 mmol), a monomer (3, 16.5 g, 47.7 mmol) and a monomer (4, 5.5 g, 12 mmol).
Rhodium Exchange Reaction:
a polymer obtained in the copolymerization is used as a carrier to prepare a supported rhodium catalyst, and a specific preparation process is the same as that in Embodiment 12 except that an applied organic acid salt of rhodium is rhodium propionate.
Carbene Insertion Reaction:
the supported rhodium catalyst prepared in the rhodium exchange reaction is used as a catalyst to prepare a penem antibiotic intermediate, and the specific raw materials and process are same as those in Embodiment 12 except the use amount of the catalyst. Based on Rh, the use amount of the supported rhodium catalyst is 0.2 mmol.

Embodiment 27

Copolymerization:
an operation method and technical conditions of copolymerization are the same as those in Embodiment 1, and what is different is the use amount of each monomer, specific use amounts of the monomers are as follows: styrene (5, 55.6 g, 534.2 mmol), a monomer (3, 10.3 g, 30 mmol) and a monomer (4, 14 g, 30 mmol).

Rhodium Exchange Reaction:

a polymer obtained in the copolymerization is used as a carrier to prepare a supported rhodium catalyst, and a specific preparation process is the same as that in Embodiment 12 except that an applied organic acid salt of rhodium is rhodium acetate.

Carbene Insertion Reaction:

the supported rhodium catalyst prepared in the rhodium exchange reaction is used as a catalyst to prepare a penem antibiotic intermediate, and the specific raw materials and process are same as those in Embodiment 12 except the use amount of the catalyst. Based on Rh, the use amount of the supported rhodium catalyst is 0.2 mmol.

The HPCL external standard yields (using a reaction with rhodium octanoate as a catalyst for reference) and the loss of rhodium of the carbene insertion reactions in Embodiment 22 to 27 are measured respectively.

A method for measuring the HPLC external standard yields of the carbene insertion reactions is as follows: in the same chromatographic conditions, an organic phase obtained by a reaction using rhodium octanoate as a catalyst is used as a standard substance, and organic phases obtained by the carbene insertion reactions are used as to-be-tested samples; the external standard yields of the carbene insertion reactions are calculated according to the following fact: the ratio of the area of the standard substance to the area of the to-be-tested samples is equal to the concentration ratio of the two. A method for measuring the loss of rhodium is as follows: the content of rhodium is measured by a traditional ICP method, so as to calculate the loss of rhodium. Measurement results are as shown in Table 3.

TABLE 3

| Test item | Embodiment 22 | Embodiment 23 | Embodiment 24 | Embodiment 25 | Embodiment 26 | Embodiment 27 |
|---|---|---|---|---|---|---|
| HPLC external standard yield | 78.5% | 90.6% | 99.4% | 94.7% | 99.8% | 100.1% |
| Rhodium loss | 2% | 0.8% | 0.2% | 0.5% | 0.2% | 0.3% |

The data above shows that the foregoing embodiments of the present disclosure have implemented the following technical effect: a carboxyl group-containing polymer provided by the present disclosure is used as a carrier of a supported metal catalyst, so that the mechanical properties of the catalyst, and the binding stability between a metal active ingredient and the carrier can be improved effectively. Thus the supported metal catalyst can be recycled without losing the activity, and the loss rate of the expensive metal in the catalyst is low. Besides, the reaction yield of a penem antibiotic intermediate may be also improved.

The above are only preferred embodiments of the present disclosure, but are not used for limiting the present disclosure. For those skilled in the art, the present disclosure may have various modifications and changes. Any modifications, equivalent replacements, improvements and the like made within the spirit and principles of the present disclosure shall be included in the scope of protection of the present disclosure.

What is claimed is:

1. A Supported metal catalyst, containing a carrier, wherein said catalyst is obtained according to Embodiment 12, said carrier is a polymer, and said polymer is prepared by polymerizing the following monomers with molar percentage:
   (1) 50%~99% of a monomer A;
   (2) 0.5%~25% of a monomer B;
   (3) 0.5%~25% of a monomer C;
   wherein the monomer A has a structure shown in formula (I):

I in the monomer A, R is phenyl;
the monomer B has one of structures shown in formula (II-1) to (II-8):

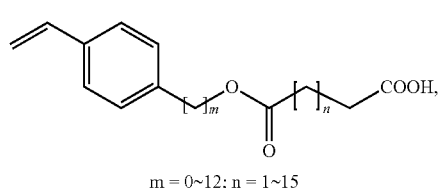

II-2

$m = 0~12; n = 1~15$ the monomer C has one of structures shown in formula (III-1), (III-2), (III-5) to (III-7):

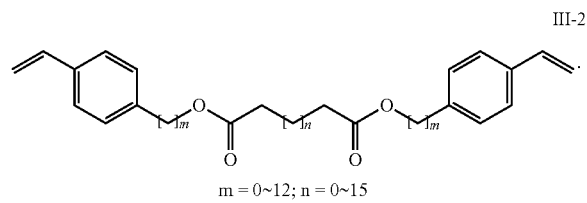

III-2

$m = 0~12; n = 0~15$

2. The catalyst according to claim 1, wherein the supported metal catalyst is a supported rhodium catalyst, a supported palladium catalyst, a supported platinum catalyst, a supported ruthenium catalyst or a supported iridium catalyst.

3. The catalyst according to claim 2, wherein the supported metal catalyst is a supported rhodium catalyst having a structure shown in the following formula (IV):

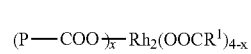

IV wherein $R^1$ is C1~C10 alkyl, P—COO— is a residue of the polymer with hydrogen removed, and x is any number of 0.1~4.0.

* * * * *

UNITED STATES PATENT AND TRADEMARK OFFICE
CERTIFICATE OF CORRECTION

PATENT NO. : 10,399,071 B2
APPLICATION NO. : 15/039189
DATED : September 3, 2019
INVENTOR(S) : Hao Hong et al.

Page 1 of 1

It is certified that error appears in the above-identified patent and that said Letters Patent is hereby corrected as shown below:

On the Title Page

Item (71) Applicants, Line 4:
"Tainjin" should be changed to -- Tianjin --

Signed and Sealed this
Twenty-second Day of October, 2019

Andrei Iancu
*Director of the United States Patent and Trademark Office*